US008486619B2

(12) United States Patent
Miller et al.

(10) Patent No.: US 8,486,619 B2
(45) Date of Patent: Jul. 16, 2013

(54) ARRAYED IMAGING REFLECTOMETRY (AIR) SENSOR CHIP COMPRISING INFLUENZA HEMAGGLUTININ (HA) POLYPEPTIDES SUITABLE FOR THE DETECTION OF ANTIVIRAL IMMUNE RESPONSES

(75) Inventors: Benjamin L. Miller, Penfield, NY (US); Tim R. Mosmann, Pittsford, NY (US); David Topham, Pittsford, NY (US); Charles R. Mace, Auburn, NY (US)

(73) Assignee: University of Rochester, Rochester, NY (US)

( * ) Notice: Subject to any disclaimer, the term of this patent is extended or adjusted under 35 U.S.C. 154(b) by 661 days.

(21) Appl. No.: 12/434,438

(22) Filed: May 1, 2009

(65) Prior Publication Data
US 2009/0275016 A1 Nov. 5, 2009

Related U.S. Application Data

(60) Provisional application No. 61/050,039, filed on May 2, 2008.

(51) Int. Cl.
*C12Q 1/70* (2006.01)
*G01N 33/552* (2006.01)
*G01N 33/549* (2006.01)
*G01N 21/00* (2006.01)
*G01B 9/02* (2006.01)

(52) U.S. Cl.
USPC ............ 435/5; 424/209.1; 436/527; 436/532; 436/164; 422/82.05

(58) Field of Classification Search
None
See application file for complete search history.

(56) References Cited

U.S. PATENT DOCUMENTS

| | | | |
|---|---|---|---|
| 4,870,023 A | 9/1989 | Fraser et al. | |
| 7,255,859 B1* | 8/2007 | Emrich et al. | 424/139.1 |
| 7,292,349 B2 | 11/2007 | Miller et al. | |
| 7,455,972 B2 | 11/2008 | Virgin | |
| 2003/0073245 A1* | 4/2003 | Shinoki et al. | 436/173 |
| 2006/0076249 A1 | 4/2006 | Meisegeier et al. | |
| 2006/0257852 A1 | 11/2006 | Rappuoli et al. | |
| 2006/0263804 A1 | 11/2006 | Robinson et al. | |
| 2007/0076214 A1 | 4/2007 | Rothberg | |
| 2007/0159325 A1 | 7/2007 | Oleynik | |
| 2007/0212375 A1 | 9/2007 | Caston et al. | |
| 2008/0031895 A1 | 2/2008 | Galarza et al. | |
| 2009/0153867 A1* | 6/2009 | Mace et al. | 356/445 |

FOREIGN PATENT DOCUMENTS

| | | |
|---|---|---|
| WO | 95/31184 A1 | 11/1995 |
| WO | 00/32228 A2 | 6/2000 |
| WO | 2007134166 A2 | 11/2007 |
| WO | WO 2007/134166 A2 * | 11/2007 |

OTHER PUBLICATIONS

Mace, C. R., et al., 2006, Theoretical and experimental analysis of arrayed imaging reflectometry as a sensitive proteomics technique, Anal. Chem. 78:5578-5583.*
Qiu, D., et al., 1992, Western blot analysis of antibody responses to influenza virion proteins, Immunol. Cell Biol. 70:181-191.*
Baggio et al., "Induced Fit of an Epitope Peptide to a Monoclonal Antibody Probed with a Novel Parallel Surface Plasmon Resonance Assay," The Journal of Biological Chemistry 280(6):4188-94 (2005).
Wegner et al., "Characterization and Optimization of Peptide Arrays for the Study of Epitope-Antibody Interactions Using Surface Plasmon Resonance Imaging," Analytical Chemistry 74(20):5161-8 (2002).
International Search Report for International Patent Application No. PCT/US09/42565 (Oct. 19, 2009).
Written Opinion for International Patent Application No. PCT/US09/42565 (Oct. 7, 2009).
European Search Report dated Apr. 20, 2011.
Callow et al., "A Re-Examination of the Single Radial Haemolysis Technique for the Assay of Influenza Anti-Neuraminidase Antibodies in Human Sera," Arc. Virol. 65:25-35 (1980).
Huber et al., "Distinct Contributions of Vaccine-Induced Immunoglobulin G1 (igG1) and IgG2a Antibodies to Protective Immunity Against Influenza," Clin. Vac. Immunol. 13(9):981-990 (2006).
Mace et al., "Label-Free, Arrayed Sensing of Immune Response to Influenza Antigens," Talanta 83:1000-1005 (2011).
MacBeath et al., "Printing Proteins as Microarrays for High-Throughput Function Determination," Science 289:1760-1763 (2000).
Mace et al., "A Theoretical and Experimental Analysis of Arrayed Imaging Reflectometry as a Sensitive Proteomics Technique," Anal Chem 78:5578-5583 (2006).
Horner et al., "A Proteomic Biosensor for Enteropathogenic *E. coli*," Biosensors and Bioelectronics 21:1659-1663 (2006).
Mace et al., "Detection of Human Proteins Using Arrayed Imaging Reflectometry," Biosensors and Bioelectronics 24:334-337 (2008).
Duthie et al., "Selection of Antigens and Development of Prototype Tests for Point-of-Care Leprosy Diagnosis," Clin Vaccine Immunol 15:1590-1597 (2008).
Xu et al., "Profiling the Humoral Immune Response to *Borrelia burgdorferi* Infection with Protein Microarrays," Microbial Pathogenesis 45:403-407 (2008).
Whelan et al., "Multiplex Immunoassay for Serological Diagnosis of Myobacterium bovis Infection in Cattle," Clin Vaccine Immunol 15:1834-1838 (2008).
Beare et al., "Candidate Antigens for Q Fever Serodiagnosis Revealed by Immunoscreening of a *Coxiella burnetti* Protein Microarray," Clin Vaccine Immunol 15:1771-1779 (2008).
Qiu et al., "Antibody Responses to Individual Proteins of SARS Coronavirus and Their Neutralization Activities," Microbes and Infection 7:882-889 (2005).
Montomoli et al., "A Method for Detection of Neuraminidase Antibody in Serum," International Congress Series 1263:524-527 (2004).
Li et al., "Protein Microarray for Profiling Antibody Responses to *Yersinia pestis* Live Vaccine," Infect. Immun. 73 (6):3734-3739 (2005).
Davies et al., "Profiling the Humoral Immune Response to Infection by Using Proteome Microarrays: High-Throughput Vaccine and Diagnostic Antigen Discovery," PNAS 102(3):547-552 (2005).

* cited by examiner

*Primary Examiner* — Jeffrey S. Parkin
(74) *Attorney, Agent, or Firm* — LeClairRyan, a Professional Corporation

(57) ABSTRACT

A sensor chip for detecting an immune response against an influenza virus, the sensor chip including a substrate having a surface and a plurality of hemagglutinin polypeptides bound to discrete locations on the surface of the substrate, each hemagglutinin polypeptide having a hemagglutinin epitope. Detection devices containing the sensor chip and methods of detecting influenza immune responses are also described herein.

14 Claims, 13 Drawing Sheets

SPR SETUP

SPR OUTPUT

```
                  1                                                          50
      ABW80979    .........M KAKLLVLLCT FTATYADTIC IGYHANNSTD TVDTVLEKNV
      EF541403    .......... MEKIVLLFAI VSLVKSDQIC IGYHANNSTE QVDTIMEKNV
      AF250479    .......... MIAIIVIAIL AAAGKSDKIC IGYHANNSTT QVDTILEKNV
      NC_004908   ........ME TISLITILLV VTASNADKIC IGHQSTNSTE TVDTLTETNV
      AY531033    MKTIIALSYI LCLVFSQKLP GNDNSTATLC LGHHAVPNGT IVKTITNDQI
      Consensus   XXXXXXXXXX XXXXXXXX1X XXaXXXdXiC iGhhaXnstt XVdTit#X#!

51                                                         100
      ABW80979    TVTHSVNLLE DSHNGKLCLL KGIAPLQLGN CSVAGWILGN PECELLISKE
      EF541403    TVTHAQDILE KKHNGKLCDL DGVKPLILRD CSVAGWLLGN PMCDEFINVP
      AF250479    TVTHSIELLE NQKEERFCKI LNKAPLDLRE CTIEGWILGN PQCDLLLGDQ
      NC_004908   PVTHAKELLH TEHNGMLCAT SLGHPLILDT CTIEGLVYGN PSCDLLLGGR
      AY531033    EVTNATELVQ SSSTGGICD. SPHQILDGEN CTLIDALLGD PQCDGFQN.K
      Consensus   XVThaX#L1X XXXXgXXCXX sXXXpLdlXX CtXXgXX1G# PqCDllXXXX 101                                                        150
      ABW80979    SWSYIVETPN PENGTCYPGY FADYEELREQ LSSVSSFERF EIFPKESSWP
      EF541403    EWSYIVEKAN PVNDLCYPGD FNDYEELKHL LSRINHFEKI QIIPKSSWSS
      AF250479    SWSYIVERPT AQNGICYPGT LNEVEELRAL IGSGERVERF EMFPQSTWQG
      NC_004908   EWSYIVERSS AVNGTCYPGN VENLEELRTL FSSASSYQRI QIFPDTTW..
      AY531033    KWDLFVERSK AYSN.CYPYD VPDYASLRSL VASSGT...L EFNNESFNWA
      Consensus   XWsyiVErsX aXngXCYPgX vX#yeeLRXL XXSXXXXXrX #XfpXsXwXX 151                                                        200
      ABW80979    NHTVTGVSAS CSHNGKSSFY RNLLWLTG.K NGLYPNLSKS YVNNKEKEVL
      EF541403    HEASLGVSSA CPYQGKSSFF RNVVWLIK.K NSTYPTIKRS YNNTNQEDLL
      AF250479    VDTNSGTTRS CPYSTGASFY RNLLWIIKTK TAEYPVIKGI YNNTGTQPIL
      NC_004908   NVTYTGTSRA CS....GSFY RSMRWLTQ.K SGFYPVQDAQ YTNNRGKSIL
      AY531033    GVTQNGTSSA CKRRSNKSFF SRLNWLTHLK YK.YPALNVT MPNNEKFDKL
      Consensus   XvTXXGtsXa CXXXXXXSF% rX$XW1tXXK XXXYPXXXXX yXNnXXXXXL 201                                                        250
      ABW80979    VLWGVHHPPN IGNQRALYHT ENAYVSVVSS HYSRRFTPEI AKRPKVRDQE
      EF541403    VLWGIHHPND AAEQTKLYQN PTTYISVGTS TLNQRLVPRI ATRSKVNGQS
      AF250479    YFWGVHHPPN TDEQDTLYGS GDRYVRMGTE SMNFAKSPEI AARPAVNGQR
      NC_004908   FVWGIHHPPT YTEQTNLYIR NDTTTSVTTE DLNRTFKPVI GPRPLVNGLQ
      AY531033    YIWGVHHPVT DSDQISLYAQ ASGRITVSTK RSQQTVIPNI GYRPRVRDIS
      Consensus   yXWG!HHPpt XX#QXXLYXX XXXXXXvXTX XX#XtXXPXI gXRPXVngXX 251                                                        300
      ABW80979    GRINYYWTLL EPGDTIIFEA NGNLIAPWYA FALSRGFGSG .IITSNAPMD
      EF541403    GRMEFFWTIL KPNDAINFES NGNFIAPEYA YKIVKKGDST .IMKSELEYG
      AF250479    GRIDYYWSVL KPGETLNVES NGNLIAPWYA YKFVNTNSKG AVFRSDLPIE
      NC_004908   GRIDYYWSVL KPGQTLRVRS NGNLIAPWYG H.VLSGGSHG RILKTDLKGG
      AY531033    SRISIYWTIV KPGDILLINS TGNLIAPRGY FKIRSGKSS. .IMRSDAPIG
      Consensus   gRIXyYWt!l KPG#tlXXXS nGNLIAPwyX XkXXsgXssg X!Xrs#lpig
```

Figure 5A

```
                   301                                                      350
ABW80979    ECDAKCQTPQ  GAINSSLPFQ  NVHPVTIGEC  PKYVRSAKLR  MVTGLRNIPS
EF541403    NCNTKCQTPM  GAINSSMPFH  NIHPLTIGEC  PKYVKSNRLV  LATGLRNSPQ
AF250479    NCDATCQTIA  GVLRTNKTFQ  NVSPLWIGEC  PKYVKSESLR  LATGLRNVPQ
NC_004908   NCVVQCQTEK  GGLNSTLPFH  NISKYAFGTC  PKYVRVNSLK  LAVGLRNVPA
AY531033    KCNSECITPN  GSIPNDKPFQ  NVNRITYGAC  PRYVKQNTLK  LATGMRNVPE
Consensus   nCXXXCqTpX  GXiXXXkpFq  N!XXXtXGXC  PkYVkX#XLk  LAtG$RN!PX 351                                                      400
ABW80979    IQ....SRGL  FGAIAGFIEG  GWTGMVDGWY  GYHHQNEQGS  GYAADQKSTQ
EF541403    RERRRKKRGL  FGAIAGFIEG  GWQGMVDGWY  GYHHSNEQGS  GYAADKESTQ
AF250479    IE....TRGL  FGAIAGFIEG  GWTGMIDGWY  GYHHENSQGS  GYAADRESTQ
NC_004908   RS....SRGL  FGAIAGFIEG  GWPGLVAGWY  GFQHSNDQGV  GMAADRDSTQ
AY531033    KQ....TRGI  FGAIAGFIEN  GWEGMVDGWY  GFRHQNSEGT  GQAADLKSTQ
Consensus   XX....tRGl  FGAIAGFIEg  GWXG$!dGWY  G%XHXNs#GX  GXAADXXSTQ 401                                                      450
ABW80979    NAINGITNKV  NSVIEKMNTQ  FTAVGKEFNK  LERRMENLNK  KVDDGFLDIW
EF541403    KAIDGVTNKV  NSIIDKMNTQ  FEAVGREFNN  LERRIENLNK  KMEDGFLDVW
AF250479    KAVNRITNKV  NSIINKMNTQ  FEAVDHEFSN  LERRIDNLNK  RMQDGFLDVW
NC_004908   KAIDKITSKV  NNIVDKMNKQ  YEIIDHEFSE  VETRLNMINN  KIDDQIQDVW
AY531033    AAINQINGKL  NRLIGKTNEK  FHQIEKEFSE  VEGRIQDLEK  YVEDTKIDLW
Consensus   kA!#XItXKv  NXi!XKmNXq  %eX!XXEFs#  vEXri#Xl#k  XX#DXXXDvW 451                                                      500
ABW80979    TYNAELLVLL  ENERTLDFHD  SNVKNLYEKV  KSQLKNNAKE  IGNGCFEFYH
EF541403    TYNAELLVLM  ENERTLDFHD  SNVKNLYDKV  RLQLRDNAKE  LGNGCFEFYH
AF250479    TYNAELLVLL  ENERTLDMHD  ANVKNLHEKV  KSQLRDNATI  LGNGCFEFWH
NC_004908   AYNAELLVLL  ENQKTLDEHD  ANVNNLYNKV  KRALGSNAME  DGKGCFELYH
AY531033    SYNAELLVAL  ENQHTIDLTD  SEMNKLFERT  KKQLRENAED  MGNGCFKIYH
Consensus   XYNAELLVlL  EN#XTlDXhD  s#vnnLX#kv  KXqLrXNAXX  XGnGCFeXyH 501                                                      550
ABW80979    KCNNECMESV  KNGTYDYPKY  SEESKLNREK  IDGVKLESMG  VYQILAIYST
EF541403    KCDNECMESV  RNGTYDYPQY  SEEARLKREE  ISGVKLESIG  IYQILSIYST
AF250479    KCDNECIESV  KNGTYDYPKY  QTESKLNRLK  IESVKLENLG  VYQILAIYST
NC_004908   KCDDQCMETI  RNGTYNRRKY  REESRLERQK  IEGVKLESEG  TYKILTIYST
AY531033    KCDNACIESI  RNGTYDHDVY  RDEALNNRFQ  IKGVELKSGY  KDWILWI.SF
Consensus   KCD#XCiEs!  rNGTY#XXkY  rXEsXl#RXk  IXgVkLesXg  XyXILXIySt 551                      580
ABW80979    VASSLVLLVS  LGAISFWMCS  NGSLQCRICI
EF541403    VASSLALAIM  VAGLSLWMCS  NGSLQCRICI
AF250479    VSSSLVLVGL  IMAMGLWMCS  NGSMQCRICI
NC_004908   VASSLVLAMG  FAAFLFWAMS  NGSCRCNICI
AY531033    AISCFLLCVA  LLGFIMWACQ  KGNIRCNICI
Consensus   vXSslvLXXX  XXafXXWacs  nGsXrCnICI
```

Figure 5B (−) control: α-Fluorescein
(+) control: α-IgG
H1: New Caledonia/1999
H3: Wyoming/2003
H6: Teal/Hong Kong/1997
$H5_1$: Hong Kong/1997
$H5_2$: Hong Kong/2003
$H5_3$: Vietnam/2004

ARRAYED IMAGING REFLECTOMETRY (AIR) SENSOR CHIP COMPRISING INFLUENZA HEMAGGLUTININ (HA) POLYPEPTIDES SUITABLE FOR THE DETECTION OF ANTIVIRAL IMMUNE RESPONSES

This application claims the benefit of U.S. Provisional Patent Application Ser. No. 61/050,039, filed May 2, 2008, which is hereby incorporated by reference in its entirety.

This invention was made with government support under grant number R24-AL054953 awarded by the National Institutes of Health. The government has certain rights in this invention.

FIELD OF THE INVENTION

This invention relates to sensor chips designed for the detection of an immune response to a particular antigen, which can be used either to detect an individual's prior exposure to a pathogen that possesses the antigen, for epidemiological purposes to survey the extent of infection among a population of individuals, or to measure the efficacy of a vaccine directed against the pathogen.

BACKGROUND OF THE INVENTION

The influenza virus is a membrane-enclosed RNA virus, whose genome consists of discretized segments of negative-sense RNA, and is primarily an infectious agent of avians and humans (Lamb et al., "The Gene Structure and Replication of Influenza Virus," *Annu Rev Biochem* 52:467-506 (1983)). The influenza proteins responsible for docking, hemagglutinin (HA), and budding, neuraminidase (NA), are anchored in the viral lipid membrane and are the major antigenic focus of the prevention and treatment of infection. There are three distinct genera of the influenza virus—denoted A, B, and C, and typified by differences in structural proteins—that cause immunological effects of variable severity (Cox et al., "The Molecular Epidemiology of Influenza Viruses," *Semin Virol* 6:359-370 (1995)), such as the typical symptoms associated with the flu (Monto et al., "Clinical Signs and Symptoms Predicting Influenza Infection," *Arch Intern Med* 160:3243-3247 (2000)). Influenzas A and B are the most immunologically relevant due to their co-circulating seasonal infectivity in human populations (Lin et al., "Recent Changes Among Human Influenza Viruses," *Virus Res* 103:47-52 (2004)), and influenza A has been responsible for all recorded pandemics. Influenza A infects many different animal species besides humans, including ducks, chickens, pigs, whales, horses, and seals. Influenza B viruses generally only infect humans.

All three types of influenza virus have genomes composed of eight different RNA helices, which encodes a single gene and are bound by a nucleoprotein that determines the viral type: A, B, or C. In effect, the influenza genome is made up of eight separate pieces of nucleic acid that can come together to form viruses with new combinations of viral genes when cells become co-infected by more than one viral type. Two of these RNA helices encode the important viral surface proteins hemagglutinin and neuraminidase, which are embedded in the lipid bilayer of a mature virus particle.

Variations in the viral hemagglutinin and neuraminidase determine the viral subtype. Hemagglutinin is responsible for entry of the virus into the host cell, while neuraminidase is important in the release of newly formed viruses from the infected cells. Antibodies to hemagglutinin can neutralize the virus and are the major determinant for immunity. Antibodies to neuraminidase do not neutralize the virus but may limit viral replication and the course of infection. Host antibodies to specific types of hemagglutinin and neuraminidase prevent and generally ameliorate future infection by the same viral strain. However, since the genetic makeup of viral strains is dynamic and ever-changing, immunity gained through successful resistance to one strain gained during an infection one year may be useless in combating a new, recombined, variant strain the next year.

Epidemics of influenza are thought to result when viral strains change over time by the process of antigenic drift. Antigenic drift (caused by mutations in the principal viral antigen genes, especially in the hemagglutinin or neuraminidase genes) results in small changes in surface antigens, and occurs essentially continuously over time. When these changes occur in the right places in the genes, they render the new antigens unrecognizable by the antibodies raised against other influenza virus strains during previous infections.

Influenza pandemics (or worldwide epidemics) occur as a result of "antigenic shift." Antigenic shift is an abrupt, major change in an influenza A virus that results from a new hemagglutinin and/or new hemagglutinin and neuraminidase protein appearing in an influenza A strain. Such shifts are generally thought to occur when a new combination of viral genomic RNAs is created, possibly in a non-human species, and that new combination is passed to humans. When such an antigenic shift occurs, most humans have little or no protection against the virus, and an infection can prove lethal.

Periodically, unique strains of the influenza virus may emerge, and the antigenic novelty of the pathogen results in enhanced rates of infectivity, transmission, and morbidity. History has shown that these influenza pandemics may be extremely deadly. For example, the "Spanish Flu" (Johnson et al., "Updating the Accounts: Global mortality of the 1918-1920 "Spanish" Influenza Pandemic," *Bull Hist Med* 76:105-115 (2002)) (H1N1; 1918-1920 upwards of 50 million deaths), the "Asian Flu" (Rajagopal et al., "Pandemic (avian) Influenza," *Semin Respir Crit. Care* 28:159-170 (2007)) (H2N2; 1957-1958, 1 million deaths), and the "Hong Kong Flu" (Shalala et al., "Collaboration in the Fight Against Infectious Diseases," *Emerg Infect Dis* 4:354-357 (1998)) (H3N2; 1968-1969, 700,000 deaths) demonstrated the efficiency of the virus and its ability to quickly spread worldwide; additionally, the rapidity in which infectious strains may emerge, and our innate resistance to them, was clearly highlighted. To combat these pandemics, the first mono- and bivalent influenza vaccines were developed in the mid-1940s, which consisted of deactivated influenza viruses (Henle et al., "Demonstration of the Efficacy of Vaccination Against Influenza Type A by Experimental Infection of Human Beings," *J Immunol* 46:163-175 (1943), Francis et al., "Protective Effect of Vaccination Against Induced Influenza A," *J Clin Invest* 24:536-546 (1945), Salk et al., "Protective Effect of Vaccination Against Induced Influenza B," *J Clin Invest* 24:547-553 (1945)). Trivalent influenza vaccines have since been become standard and consist of three deactivated strains (Halperin et al., "Safety and Immunogenicity of a Trivalent, Inactivated, Mammalian Cell Culture-derived Influenza Vaccine in Healthy Adults, Seniors, and Children," *Vaccine* 20:1240-1247 (2002)), or three live, attenuated strains (Belshe et al., "The Efficacy of Live Attenuated, Cold-adapted, Trivalent, Intranasal Influenzavirus Vaccine in Children," *New Engl J Med* 338:1405-1412 (1998))—two of influenza A and one of influenza B—in order to provide broader preventative measures against co-circulating seasonal strains. Since these initial efforts, much research has been performed towards developing improved, more enveloping vaccines based on recombinant technology to not only immunize against current viral strains (Kilbourne et al., "Future Influenza Vaccines and the Use of Genetic Recombinants," *Bull World Health Org* 41:643-645 (1969), Webby et al., "Are We Ready for Pandemic Influenza?," *Science* 302:1519-1522 (2003), Treanor et al., "Safety and Immunogenicity of a Baculovirus-Expressed Hemagglutinin Influenza Vaccine: A Randomized Controlled Trial," *J Am Med Assoc* 297:1577-1582 (2007)), but also provide protection against past epidemic strains as well.

Avian influenza, of the H5N1 designation, is currently the subject of major international research efforts. Past influenza pandemics have proven that in the absence of proper safeguards, new and highly pathogenic strains of influenza can be extremely deadly. With the rise in the global population and the advent of international travel and commerce, the repercussions of a pandemic would be devastating. Since it was initially isolated in 1997 (de Jong et al., "A Pandemic Warning?" *Nature* 389:554 (1997)), there have been a reported 380 cases of H5N1 that have resulted in 240 deaths (World Health Organization, "*Epidemic and Pandemic Alert and Response: Avian Influenza*," accessed online from the WHO on Apr. 16, 2008). The majority of these reported cases are transmitted from avians to humans, but isolated cases of human-to-human transmission have been reported (Ungchusak et al, "Probable Person-to-Person Transmission of Avian Influenza A (H5N1)," *N Engl J Med* 352:333-340 (2005)).

Very recently, there have been reports of an H1N1, type A, strain of swine influenza that has unique genetic properties and is capable of human-to-human transmission. The initial outbreak appeared in Mexico, but cases have now been reported in a number of urban centers across the United States and elsewhere in the world. As of Apr. 30, 2009, the World Health Organization has raised the Alert Level to Phase 5.

Vaccines are essential as preventative measures against disease, but traditional drug-based therapeutics are also required in the event that the vaccine supply is limited or not yet available, scenarios that are especially worrisome in highly virulent pandemic viral strains such as with avian influenza H5N1 (Kilpatrick et al., "Predicting the Global Spread of H5N1 Avian Influenza," *Proc Natl Acad Sci USA* 103:19368-19373 (2006)). For example, neuraminidase, the influenza enzyme that controls the release of the newly packaged virus from the host cell membrane (Wagner et al., "Interdependence of Hemagglutinin Glycosylation Neuraminidase as Regulators of Influenza Virus Growth: A Study by Reverse Genetics," *J Virol* 74:6316-6323 (2000)), is an attractive drug target in the influenza lifecycle. Oseltamivir (TAMIFLU™) (Kim et al., "Influenza Neuraminidase Inhibitors Possessing a Novel Hydrophobic Interaction in the Enzyme Active Site Design, Synthesis, and Structural Analysis of Carboxylic Acid Sialic Acid Analogues with Potent Anti-Influenza Activity," *J Am Chem Soc* 119:681-690 (1997)) is an orally active antiviral that acts as a transition state mimic of the active site of neuraminidase. It is currently suggested that world centers begin stockpiling supplies of TAMIFLU™ (and other antivirals, such as Zanamivir (Itzstein et al., "Rational Design of Potent Sialidase-Based Inhibitors of Influenza Virus Replication," *Nature* 363:418-423 (1993)) in the event of a sudden pandemic (Moscona et al., "Neuraminidase Inhibitors for Influenza," *New Engl J Med* 353:1363-1373 (2005)). While antivirals are capable therapies, preventative rather than reactive measures will ultimately ensure long-term success against deadly influenza virus pandemics since drug-resistant forms of influenza are readily appearing (de Jong et al., "Oseltamivir Resistance During Treatment of Influenza A (H5N1) Infection," *New Engl J Med* 353:2667-2672 (2005)).

An ancillary development stemming from researchers' ability to produce and amplify recombinant proteins, and the genes from which they are encoded, is the high-throughput microarray. While initial applications of high-throughput screening focused on genomic arrays (Schena et al., "Quantitative Monitoring of Gene Expression Patterns With a Complementary DNA Microarray," *Science* 270:467-470 (1995), Lipshutz et al., "High density Synthetic Oligonucleotide Arrays," *Nat Genet.* 21:20-24 (1999)), the protein microarray has found a variety of significant uses as well. For example, proteome profiling via protein microarrays has unveiled a myriad of novel interactions (MacBeath et al., "Printing Proteins as Microarrays for High-Throughput Function Determination," *Science* 289:1760-1763 (2000), Michaud et al., "Analyzing Antibody Specificity With Whole Proteome Microarrays," *Nat Biotech* 21:1509-1512 (2003), Chan et al., "Protein Microarrays for Multiplexed Analysis of Signal Transduction Pathways," *Nat Med* 10: 1390-1396 (2004)). Protein microarrays have been used to discover antigenic proteins and monitor human immunological responses to them (Davies et al., "Profiling the Humoral Immune Response to Infection by Using Proteome Microarrays: High-Throughput Vaccine and Diagnostic Antigen Discovery," *Proc Natl Acad Sci USA* 102:547-552 (2005), Li et al., "Protein Microarray for Profiling Antibody Responses to *Yersinia pestis* Live Vaccine," *Infect Immun* 73:3734-3739 (2005), Qiu et al., "Antibody Responses to Individual Proteins of SARS Coronavirus and Their Neutralization Activities," *Microbes Infect* 7:882-889 (2005)). This tactic has not been used previously for immobilization of multiple isoforms of the influenza antigen hemagglutinin. Moreover, in each of these reports, detection was achieved using labeled reagents.

It would be desirable to provide an array of immobilized antigen isoforms that can be used to screen for antibodies against infectious agents and vaccines involving multiple similar specificities, e.g., distinguishing between different strains of an infectious agent such as influenza based on the immune response generated by these infectious agents, or vaccines against them, using unlabeled reagents. In view of the possibility of influenza pandemic, it would also be desirable to develop a system capable of screening putative vaccine therapies for efficacy and/or cross-protection against various strains of influenza. Furthermore, a system able to rapidly screen for the presence of avian influenza or other strains in wildlife and livestock would be of considerable utility in monitoring the status and spread of the disease.

The present invention is directed to overcoming these and other deficiencies in the art.

SUMMARY OF THE INVENTION

A first aspect of the present invention relates to a sensor chip for detecting an immune response against an influenza virus. The sensor chip includes a substrate having a surface and a plurality of hemagglutinin polypeptides bound to discrete locations on the surface of the substrate, each hemagglutinin polypeptide having a hemagglutinin epitope, preferably the immunodominant epitope thereof. The sensor chip may optionally include a plurality of neuraminidase polypeptides bound to discrete locations on the surface of the substrate, each neuraminidase polypeptide having a neuraminidase epitope.

In preferred embodiments, the sensor chip is suitable for use in an Arrayed Imaging Reflectometry ("AIR") detection system, a surface plasmon resonance ("SPR") detection system, a Brewster Angle Straddle Interferometry ("BASI") detection system, and ellipsometry detection systems.

A second aspect of the present invention relates to a detection system that includes a sensor chip according to the first aspect of the present invention. The detection system preferably includes a light source that is positioned to illuminate the chip and a detector that is positioned to detect light reflected from the surface of the chip, and thereby determine whether an antibody binds to the hemagglutinin polypeptide.

A third aspect of the present invention relates to a flow cell useful for detecting anti-influenza antibodies in a sample. The flow cell includes a base having an inlet and an outlet; a light transmissive cover mounted to the base in a substantially fluid-tight manner, and forming with the base a compartment through which fluid may pass from the inlet to the outlet; and a sensor chip according to the first aspect of the present invention, which is positioned in the compartment and exposed through the light transmissive cover to incident light, whereby incident light used to illuminate the chip surface at an appropriate angle of incidence achieves a condition of near perfect destructive interference in the absence of antibody binding to a hemagglutinin polypeptide and a substantial change in light reflectivity in the presence of antibody binding to a hemagglutinin polypeptide.

A fourth aspect of the present invention relates to a detection system that includes: a flow cell according to the third aspect of the present invention; a fluid sample source in fluid communication with the inlet of the flow cell; a light source that is positioned to illuminate the chip; and a detector that is positioned to detect light reflected from the surface of the chip, wherein the angle of incidence of the illuminating light is suitable to produce a condition of near perfect destructive interference in the absence of antibody binding to a hemagglutinin polypeptide and a substantial change in light reflectivity in the presence of antibody binding to a hemagglutinin polypeptide.

A fifth aspect of the present invention relates to a method for sensing an anti-influenza antibody in a sample. This method includes providing a detection system according to the second or fourth aspects of the present invention; directing light at a surface of the sensor chip; contacting the sensor chip with a sample under conditions effective to allow an anti-influenza antibody in the sample to bind specifically to a hemagglutinin polypeptide recognized by the antibody; and detecting light reflected from the chip under conditions effective to identify hemagglutinin polypeptides bound by an antibody of the sample.

In preferred embodiments, detection is carried out using an AIR detection system, an SPR detection system, a BASI detection system, or ellipsometry detection system.

A sixth aspect of the present invention relates to a method for sensing an anti-influenza antibody using the detection system according to the fourth aspect of the present invention, which method includes the steps of directing light at the sensor chip in a manner effective to result in a condition of near perfect destructive interference; introducing a fluid sample into the flow cell; measuring light reflected from the chip; and providing an output identifying the hemagglutinin polypeptides bound by an antibody of the fluid sample based on the measured reflected light.

A seventh aspect of the present invention relates to a method for screening efficacy of an influenza vaccine. This method includes the steps of administering an influenza vaccine to one or more individuals; obtaining a serum sample for the one or more individuals; and performing the method according to the fifth or sixth aspects of the present invention to measure the anti-influenza immune response generated by the influenza vaccine.

The sensor chips of the present invention, containing arrays of influenza hemagglutinin polypeptides, have been demonstrated to produce detection results using a label-free, "reagentless" technique in less than 30 minutes, and the results are shown to be consistent with those derived via a comparative ELISA assay, which takes longer to perform and requires additional labeled reagents to be introduced following reaction of the sample to the sensor chip. Consequently, the present invention offers a faster, reliable detection system for measuring vaccine efficacy and cross-reactivity for influenza virus strains. The examples herein demonstrate that with implementation via an AIR detection system, antibody titers over a wider dynamic range can be screened in a single experiment as compared to ELISA.

BRIEF DESCRIPTION OF THE DRAWINGS

FIGS. 5A-B are an alignment of hemagglutinin sequences from Genbank Accession ABW80979 (strain A/New Calcdonia/20/1999, H1N1) (SEQ ID NO: 1), AY531033 (strain A/Wyoming/3/2003, H3N2) (SEQ ID NO: 2), EF541403 (strain A/Vietnam/1203/2004, H5N1) (SEQ ID NO: 3), AF250479 (strain A/Teal/Hong Kong/W312/199, H6N1) (SEQ ID NO: 4), and NC_004908 (strain A/Hong Kong/1073/1999, H9N2) (SEQ ID NO: 5), each of which is hereby incorporated by reference in its entirety). The alignment was prepared using Multalin version 5.4.1 (Corpet, "Multiple Sequence Alignment with Hierarchical Clustering," *Nucl

DETAILED DESCRIPTION OF THE INVENTION

One aspect of the present invention concerns a sensor chip that is useful for detecting an immune response against an influenza virus. The sensor chip includes a substrate having a surface and a plurality of hemagglutinin polypeptides bound to discrete locations on the surface of the substrate, each hemagglutinin polypeptide having a hemagglutinin epitope, preferably the immunodominant epitope thereof.

The overall design and construction of the sensor chip can be varied according to the particular detection system in which it is to be employed. These include, for example and without limitation, sensors designed for use with AIR detection systems, SPR detection systems, BASI detection systems, and ellipsometry detection systems, as well as any other label-free or fluorescence labeled array technique.

Figure 1:
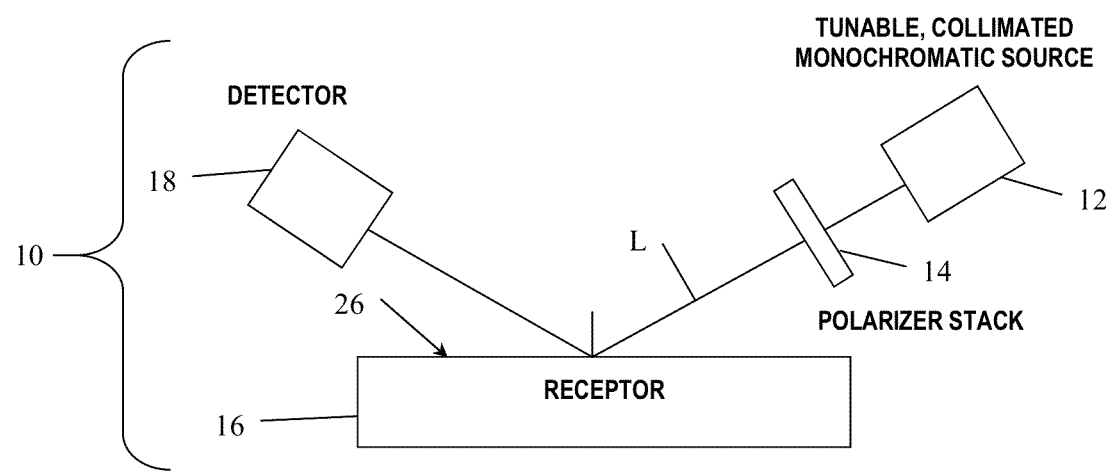
FIG. 1 is a schematic illustration of an AIR detection system.

An AIR detection system is described in U.S. Pat. No. 7,292,349 to Miller et al., which is hereby incorporated by reference in its entirety. This setup is illustrated in FIG. 1. The system 10 includes a light source 12, a polarizer 14, a receptor 16 (i.e., the functionalized sensor chip of the present invention), and a detector 18. The light source 12 generates and transmits a light (L) at a set wavelength towards a surface of the receptor. One or more lenses and filters can be employed to optimize the system. AIR exploits interference between reflections from the medium/coating and coating/substrate interfaces on the receptor, exhibiting changes in reflectivity upon binding of biomolecules to the coating. In practice, using a silicon wafer having an oxide coating, judicious choice of incident angle and wavelength can be used with s-polarized light to obtain near complete destructive interference (i.e., reflectivity that is preferably less than about $10^{-5}$ or even $10^{-6}$ under some circumstances) in the absence of a target, in this case the anti-hemagglutinin antibodies. The condition of near complete (or near perfect) destructive interference is removed upon target binding. Thus, highly sensitive detection of even small quantities of anti-hemagglutinin antibodies is possible.

While AIR using s-polarized light has proven to be a highly sensitive, simple analytical method for the quantitative detection of a variety of biomolecular analytes, the system described in the above-referenced U.S. Pat. No. 7,292,349 to Miller et al. is much more easily carried out in a dry state, that is, with an air/oxide interface rather than with an aqueous/oxide interface. An improved system for performing AIR in an aqueous environment is described in co-pending U.S. patent application Ser. No. 12/261,818 to Mace et al., and PCT International Patent Application No. PCT/2008/081804 to Mace et al., which are hereby incorporated by reference in their entirety. Basically, the flow cell as described therein allows for coupling of the s-polarized light into the aqueous environment for detection of target binding. Use of this same flow cell, containing a sensor chip functionalized with the plurality of hemagglutinin polypeptides, in contemplated herein.

Figure 2:
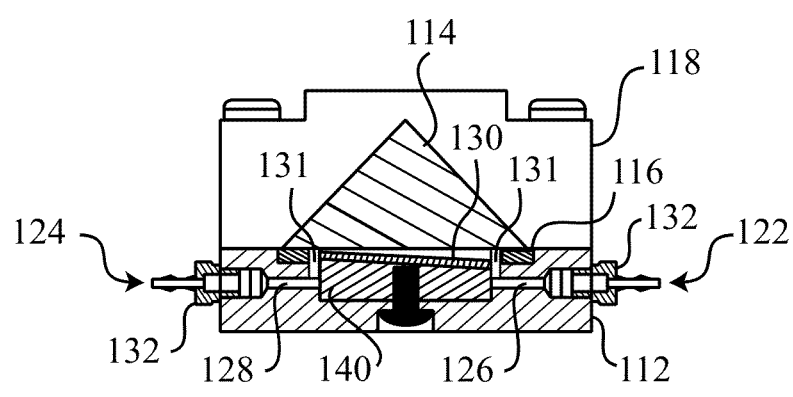
FIG. 2 is a cross-sectional view a flow cell of the invention which includes a sensor chip suitable for use in an AIR detection system for aqueous environments.

The flow cell is illustrated in FIG. 2. The flow cell includes a base 112, a light transmissive cover 114 in the form of a 90° prism, a gasket 116 positioned between the base and cover, and one or more mounting braces 118 that are utilized to secure the base and cover in a substantially fluid-tight manner. The base 112 includes a well 120 formed in one face thereof, as well as inlet 122 and outlet 124 that communicate with the well via passages 126 and 128, respectively. Inlet 122 and outlet 124 are formed on opposite ends of the base such that the passages 126 and 128 that communicate with the well 120 ensure fluid flow over chip 130 when it is placed in the well. To assist with fluid flow in this respect, a notch 131 is formed in the sidewall of well 120 at each end of the well such that fluid can easily flow into the well from passage 126 and from the well via passage 128. The passages 126 and 128 are preferably provided with fittings 132 that allow conduits or other forms of tubing to be coupled to the flow cell. For example, the fluid sample source can be coupled to the inlet 122 and the outlet 124 can be coupled to additional fluid analyzers or simply to a waste reservoir. The chip 130 is preferably supported in the well 120 by an angled chip support 140.

In both the wet and dry AIR systems, the sensor chip has the same fundamental construction, with a substrate, one or more coating layers on the substrate, and then the probe molecules—in this case the hemagglutinin polypeptides—bound to the coating surface. As described in the above-referenced U.S. Pat. No. 7,292,349 to Miller et al., U.S. patent application Ser. No. 12/261,818 to Mace et al., and PCT International Patent Application No. PCT/2008/081804 to Mace et al., a number of different materials can be selected for the substrate and coating(s). Any suitable combination of substrates and coatings is contemplated for the sensor chip to be used in an AIR detection system.

The BASI detection system is described in U.S. Patent Publication No. 20070076214 to Rothberg, which is hereby incorporated by reference in its entirety. The BASI system, like the AIR system, exploits interference between reflections from the medium/coating and coating/substrate interfaces, and exhibits changes in reflectivity upon binding of biomolecules to the coating. The basic design of the system is similar to that illustrated in FIG. 1 (for AIR), but the structure of the sensor chip differs. The BASI system is functional with any substrate/coating combinations where the coating is very thin (e.g., a native oxide film on silicon) and when the incidence angle on one of two interfaces (substrate/coating or coating/medium) is greater than its Brewster angle and the incidence angle on the other of the two interfaces is less than its Brewster angle. Unlike AIR systems being commercially developed for use with incident s-polarized light, the BASI system relies on the detection of p-polarized light. As a result of using Brewster angle straddle and p-polarized light, where the coating thickness is $\ll \lambda$, a phase flip of the reflected polarization allows nearly complete destructive interference (where reflectivity is preferably less than about $10^{-4}$ or even $10^{-5}$ in the absence of target binding). As with the AIR detection system, sensitive detection of even small quantities of anti-hemagglutinin antibodies is possible.

Figure 3:
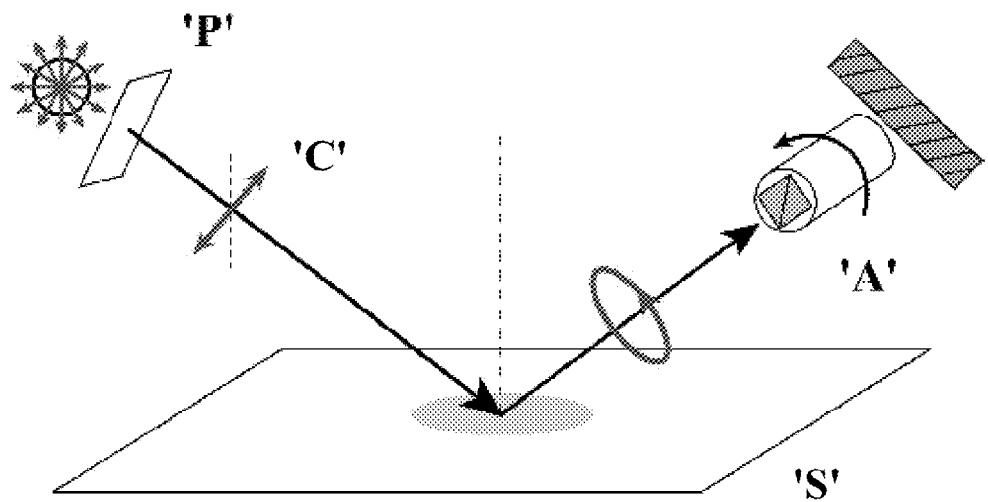
FIG. 3 is a schematic illustration of an ellipsometry detection system.

Ellipsometric detection systems measure the polarization component of reflected light as a measure of changes in coating thickness on the surface of the sensor chip. Ellipsometry sensitively measures the change of the state of polarization when electromagnetic radiation is reflected or transmitted by a sample. A classical embodiment of such an ellipsometric detection system, illustrated in FIG. 3, includes a light source that emits a collimated light beam passing a variable polarization controller given by the combination of a linear polarizer (P) and a compensator in the form of a quarter-wave plate (C). The polarized light beam is incident on the sensor surface (S) under a known oblique angle, reflected from the sample surface and analyzed by a second linear polarizer coupled to a suitable photodetector (A, collectively). In this ellipsometer setup, the measurement may be done by changing the azimuths of the components P and A, while the optical axis of C is kept at a constant azimuth, e.g., at 45° with respect to the plane of incidence, until the photodetector receives a minimum of intensity. The azimuthal angles of the components P, C and A for this "nulling" condition may be used to calculate the ellipsometric angles Delta and Psi, which are specific for the optical parameters of the sample at a given angle of incidence and wavelength of light. Using a suitable optical model and numerical regression, the quantities Delta and Psi may be recalculated in terms of the thickness of the optical layer, or changes thereof during a growth process. The application of ellipsometry for monitoring of binding reactions of biological molecules dates back to 1942 (Rothen et al., "Serological Reactions of Protein Films and Denatured Proteins," *J. Exp. Med.* 76:437 (1942), which is herby incorporated by reference in its entirety), where the amount of adsorbed biological material at a surface during a binding reaction may be recalculated from the quantities Delta and Psi.

Imaging ellipsometry, as described for example in U.S. Pat. No. 5,076,696 to Cohn et al., which is hereby incorporated by reference in its entirety, uses spatially resolving detector and imaging optics to allow for a massively parallel measurement of ellipsometric data, e.g., in the form of Delta and/or Psi maps. Such maps may in turn be converted into surface maps of layer thickness, optical index of refraction, chemical composition or the amount of adsorbed material for each spot on an array. Imaging ellipsometry with its intrinsic parallel detection scheme may be used advantageously as a detection technique for these so-called biochips, microarrays or microplates (Eing et al., *Imaging Ellipsometry in Biotechnology*, ISBN 3-9807279-6-3 (2002), which is hereby incorporated by reference in its entirety).

Imaging ellipsometry has been demonstrated with light employed for the measurement impinging on the surface to be measured coming from the ambient medium. Other measurement setups are based on total internal reflection as described for example in U.S. Pat. No. 6,594,011 to Kempen, which is hereby incorporated by reference in its entirety. Here, the light from a light source is directed through an internal reflection element to reflect off the specimen to be detected.

Figure 4A:
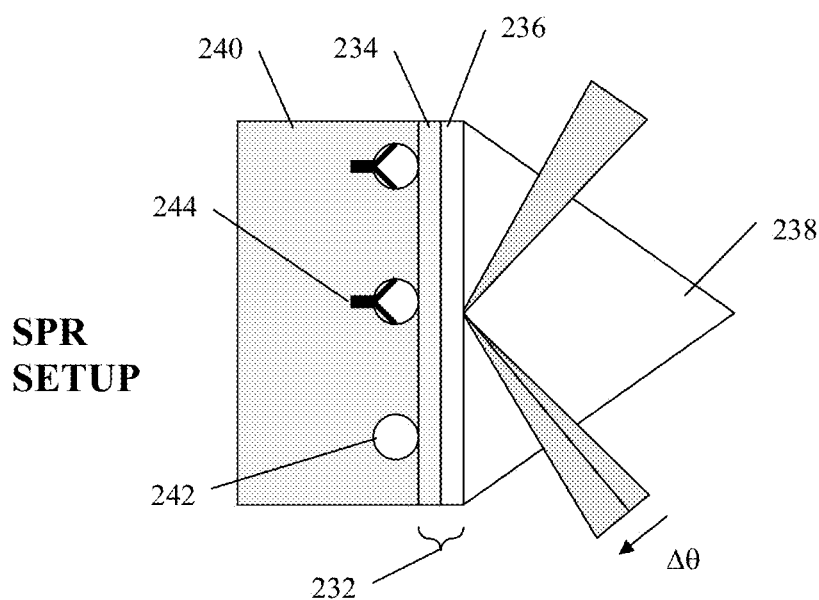
FIG. 4A is a schematic illustration of an SPR detection system.
Figure 4B:
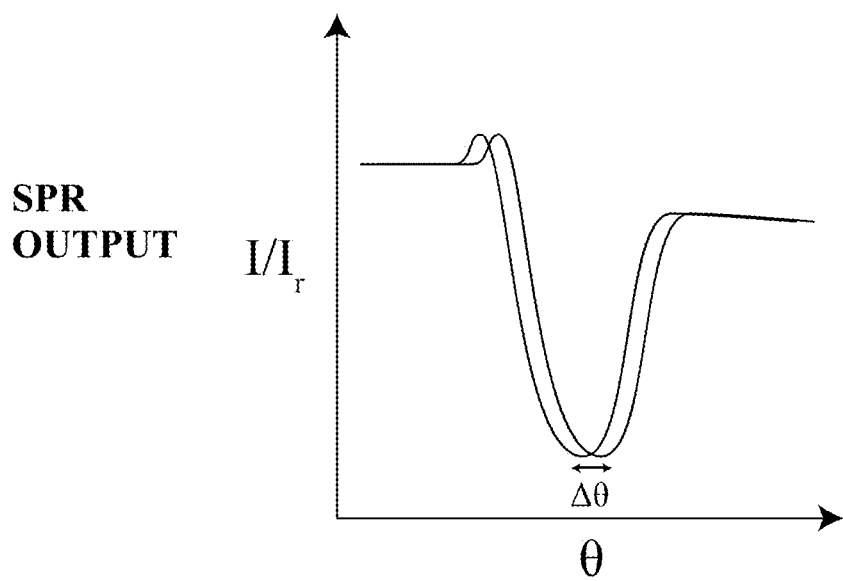
FIG. 4B illustrates the output of SPR.

Enhancement of the detection signal can be achieved using SPR ellipsometry, illustrated in FIG. 4A. The substrate 232 employed during SPR ellipsometry uses a thin metal layer 234 to allow the excitation and propagation of surface plasmons. While one side of the metal layer 234 is in contact with a transparent support structure 236, usually attached to a prism 238 allowing light to couple-in under an oblique angle, the other side of the layer is exposed to the ambient medium 240. Changes in the optical index of refraction in the ambient by the formation of an adsorbent layer (e.g., antibodies 244 binding to surface-bound hemagglutinin polypeptide 242) are monitored as a shift in the angle of incidence ($\Delta\theta$) that generates surface plasmon resonance, causing a change of reflected light intensity (see FIG. 4B). For SPR based sensors it is known that an intermediate dielectric layer between the metal film and the probed surface may act as a means to further increase the sensitivity.

One exemplary SPR substrate is described in U.S. Pat. No. 7,332,329 to Wark et al., which is hereby incorporated by reference in its entirety. This SPR substrate is particularly suited for biomolecular arrays of hemagglutinin polypeptides, where the substrate includes a plurality of a metallic islands surrounded by a hydrophobic layer or a dielectric material, and the hemagglutinin polypeptides are bound to the metallic islands.

Regardless of the sensor chip substrate or the detection system in which the substrate is intended to be used, the sensor chip includes a plurality of hemagluttinin polypeptides bound to the surface of the sensor chip. Each hemagluttinin polypeptide bound to the surface of the sensor chip can be a full length protein or a polypeptide fragment thereof.

A trait inherent to all biosensors, regardless of labeling status or means of signal transduction, is probe immobilization. The role of the terminal hydroxyl of a silicon dioxide surface is highly flexible as it may act as a nucleophile (Bikiaris et al., "Compatibilisation effect of PP-g-MA copolymer on iPP/SiO2 nanocomposites prepared by melt mixing," *Eur Polym J* 41:1965-1978 (2005); Tripp et al., "Chemical Attachment of Chlorosilanes to Silica: A Two-step Amine-promoted Reaction," *J Phys Chem* 97:5693-5698 (1993), each of which is hereby incorporated by reference in its entirety) or support adsorption. For this reason, silicon dioxide is readily derivatized through a variety of chemical methods. These chemical reactions result in the effective transformation of the hydroxyl group to any of a number of chemical functionalities including, but not certainly not limited to, amines (Huang et al., "Directed Assembly of One-dimensional Nanostructures Into Functional Networks," *Science* 291: 630-633 (2001), which is hereby incorporated by reference in its entirety) or halides (Hergenrother et al., "Small-molecule Microarrays: Covalent Attachment and Screening of Alcohol-containing Small Molecules on Glass Slides," *J Am Chem Soc* 122: 7849-7850 (2001), which is hereby incorporated by reference in its entirety). From each initial reaction, a secondary chemical can be added to further alter the surface reactivity or probes may be directly coupled. Moreover, a multitude of functionalized silanes, molecules that couple to and self-assemble on silicon dioxide (Onclin et al., "Engineering Silicon Oxide Surfaces Using Self-assembled Monolayers," *Angew Chemie Int Ed* 44:2-24 (2005), each of which is hereby incorporated by reference in its entirety), are commercially available, and may confer a diverse chemical landscape to the surface of the substrate (amines, epoxides, alkenes, etc.). A number of these approaches are generally described in U.S. Pat. No. 7,226,733 to Chan et al. and U.S. Pat. No. 7,292,349 to Miller et al., each of which is hereby incorporated by reference in its entirety.

U.S. Provisional Patent Application Ser. No. 61/101,831 to Mace et al., which is hereby incorporated by reference in its entirety, teaches the use of a non-nucleophilic additive in a formulation containing a probe molecule to be bound to an array surface. The non-nucleophilic additive is used in an amount effective to avoid or reduce the severity of surface morphological anomalies caused by non-homogeneous distribution of the reactant across a spot on the array where the reactant is bound. These surface morphological anomalies include bright center spots and "coffee stain" rings (or halos) that can interfere with accurate detection of target molecule binding at a particular spot. In other words, the use of effective amounts of the non-nucleophilic additive promotes substantially homogeneous distribution of the reactant across each of the spots on the array where the probe is located. By homogeneous distribution, it is intended that the variance of reactant concentration across the surface of a spot is minimized (relative to spots prepared in the absence of the non-nucleophilic additives). Stated another way, there is preferably less than about 10 percent pixel variation across the array spot, more preferably less than 5 percent variation, most preferably less than about 3 percent variation, 2 percent variation, or even less than about 1 percent variation.

Any effective amount of non-nucleophilic additive can be used. Typically, such an effective amount is between about 0.001 to about 3 percent v/v, more preferably between about 0.01 to about 1 percent v/v.

One embodiment of the non-nucleophilic additive includes compounds having a structure of formula (I) as follows:

$$R^1-O-[(CH_2)_mO]_n-R^2 \quad (1)$$

where, n is an integer from 0 to about 250; m is an integer from 1 to 3, preferably 1 or 2; and $R^1$ and $R^2$ are independently selected from the group of a C1 to C3 alkyl, or $R^1$ and $R^2$ together form a C1 to C3 alkyl, in which case the compound of formula (I) has a cyclic structure. $R^1$ and $R^2$ are preferably methyl or ethyl, or together form an ethyl group. These additives preferably have a molecular weight that is about 5000 Da or less, more preferably about 4000 Da or less, or about 3000 Da or less, most preferably about 2000 Da or less, or even about 1000 Da or less. Exemplary non-nucleophilic additives of formula (I) include, without limitation, crown ethers (18-Crown-6,15-Crown-5, 12 Crown-4, etc.), bis(2-methoxyethyl)ether, dialkyl ethers, and polyethylene glycol.

According to another embodiment, the non-nucleophilic additive is dimethylsulfoxide (DMSO).

The benefit of employing the non-nucleophilic additives, which do not participate in the chemical coupling of a reactant (or probe precursor) to the functionalized chip substrate, is that the additives promote better dispersion of the probe molecules across their respective discrete locations on the array. This improved dispersion consequently minimizes or entirely avoids the presence of surface morphological anomalies that can decrease the sensitivity of the detection system. As a result, improved sensitivity for the detection of target molecules can be achieved.

Hemagglutinin, a 222 kDa transmembrane homotrimer, is the influenza antigen responsible for mediating host cell recognition via sialic acid receptors (Copeland et al., "Assembly of Influenza Hemagglutinin Trimers and Its Role in Intracellular Transport," *J Cell Biol* 103:1179-1191 (1986), which is hereby incorporated by reference in its entirety). Currently, there are sixteen major HA isoforms that have been identified (Fouchier et al., "Characterization of a Novel Influenza A Virus Hemagglutinin Subtype (H16) Obtained from Blackheaded Gulls," *J Virol* 79:2814-2822 (2005), which is hereby incorporated by reference in its entirety), and isolated viral serotypes are, along with neuraminidase, categorized based on this determinant. When host contact has been made, the cell attempts to endocytose the virus. The lower pH environment of the endosome causes a drastic structural rearrangement in HA (Skehel et al., "Changes in the confirmation of Influenza Virus Hemagglutinin at the pH Optimum of Virus-mediated Membrane Fusion," *Proc Natl Acad Soc USA* 79:968-972 (1982), which is hereby incorporated by reference in its entirety) that results in membrane fusion and, ultimately, delivery of the viral payload (Skehel et al., "Receptor Binding and Membrane Fusion in Virus Entry: the Influenza Hemagglutinin," *Annu Rev Biochem* 69:531-569 (2000), which is hereby incorporated by reference in its entirety).

The region of the viral RNA genome that encodes for HA is highly susceptible to mutation (Plotkin et al., "Codon Bias and Frequency-dependent Selection on the Hemagglutinin Epitopes of Influenza A Virus," *Proc Natl Acad Sci USA* 100:7152-7157 (2003), which is hereby incorporated by reference in its entirety), and is the primary cause for the influenza virus' ability to evade host defenses. Evolution of this type is categorized as either 'antigenic drift' or 'antigenic shift': 'Antigenic drift' is the natural accumulation of mutations in genes that encode antigenic proteins, whereby an alteration in the immunological properties of the antigen results (Jin et al., "Two Residues in the Hemagglutinin of A/Fujian/411/02-like Influenza Viruses are Responsible for Antigenic Drift from A/Panama/2007/99," *Virology* 336:113-119 (2005), which is hereby incorporated by reference in its entirety). 'Antigenic shift', on the other hand, is a drastic genetic recombination that occurs between two viral strains simultaneously infecting a host cell, thus generating an immunologically distinct antigen (Laver et al., "Studies on the Origin of Pandemic Influenza III. Evidence Implicating Duck and Equine Influenza Viruses as Possible Progenitors of the Hong Strain of Human Influenza," *Virology* 51:383-391 (1973), which is hereby incorporated by reference in its entirety). By understanding and anticipating both evolutionary pathways, it is then possible to phylogenetically trace the progression of one influenza serotype to another through sequencing antigenic Determinants (Lindstrom et al., "Genetic Analysis of Human H2N2 and Early H3N2 Influenza Viruses, 1957-1972: Evidence for Genetic Divergence and Multiple Reassortment Events," *Virology* 328:101-119 (2004), which is hereby incorporated by reference in its entirety). For example, the divergence of the human pandemic H2N2 virus to pandemic H3N2 virus was mapped in this manner (Scholtissek, et al., "On the Origin of the Human Influenza Virus Subtypes H2N2 and H3N2," *Virology* 87:13-20 (1978), which is hereby incorporated by reference in its entirety).

The sensor chip arrays of the present invention are intended to include any two or more hemagglutinin polypeptides, but preferably any one or more H1 polypeptides (such as those from H1N1-H1N9), any one or more H2 polypeptides (such as those from H2N1-H2N9), any one or more H3 polypeptides (such as those from H3N1-H3N9), any one or more H4 polypeptides (such as those from H4N1-H4N9), any one or more H5 polypeptides (such as those from H5N1-H5N9), any one or more H6 polypeptides (such as those from H6N1-H6N9), any one or more H7 polypeptides (such as those from H7N1-H7N9), any one or more H8 polypeptides (such as those from H8N1-H8N9), any one or more H9 polypeptides (such as those from H9N1-H9N9), any one or more H10 polypeptides (such as those from H10N1-H10N9), any one or more H11 polypeptides (such as those from H11N1-H11N9), any one or more H12 polypeptides (such as those from H12N1-H12N9), any one or more H13 polypeptides (such as those from H13N1-H13N9), any one or more H14 polypeptides (such as those from H14N1-H14N9), any one or more H15 polypeptides (such as those from H15N1-H15N9), any one or more H16 polypeptides (such as those from H16N1-H16N9), and all possible combinations thereof. Any newly discovered hemagglutinin variants can also be incorporated onto the sensor chip of the present invention.

In addition to hemagglutinin polypeptides, the sensor chip arrays of the present invention can also include any two or more neuraminidase polypeptides. Preferably, the sensor chip arrays include any one or more N1 polypeptides (such as those from H1N1-H16N1), any one or more N2 polypeptides (such as those from H1N2-H16N2), any one or more N3 polypeptides (such as those from H1N3-H16N3), any one or more N4 polypeptides (such as those from H1N4-H16N4), any one or more N5 polypeptides (such as those from H1N5-H16N5), any one or more N6 polypeptides (such as those from H1N6-H16N6), any one or more N7 polypeptides (such as those from H1N7-H16N7), any one or more N8 polypeptides (such as those from H1N8-H16N8), any one or more N9 polypeptides (such as those from H1N9-H16N9), and all possible combinations thereof. Any newly discovered neuraminidase variants can also be incorporated onto the sensor chip array of the present invention.

As is appreciated by persons of skill in the art, antigens subject to post-translational modifications such a glycosylation may also be included on the array. For example, recombinant expression of hemagglutinin or neuraminidase polypeptides (to be bound to the array surface) in mammalian cells or Baculovirus cells should result in their glycosylation.

As will be appreciated by those of skill in the art, the amount of hemagglutinin or neuraminidase bound to each discreet location on the chip can be optimized based on the surface area of the location where detection is to occur. By way of example, it is believed that optimal results can be achieved with a concentration of hemagglutinin or neuraminidase polypeptide per location of about 100 ng/mm$^2$ to about 100 ng/mm$^2$, preferably about 1 pg/mm$^2$ to about 10 ng/mm$^2$.

The experimental HA arrays (described below) that are utilized in the present invention are of distinct isoforms and isolates. This does not, however, prohibit the cross-reactivity of specifically raised antisera to surface-immobilized recombinant hemagglutinins. Therefore, to obtain a molecular understanding of the subtle differences between the hemagglutinins in the antigen array, a multiple amino acid sequence alignment of hemagglutinins from the H1N1, H3N2, H5N1, H6N1, and H9N2 strains (obtained from Genbank—see Materials and Methods, infra) was performed. As shown in FIG. 5, these five protein sequences were found to have complete identity of 24.5% of amino acids and an additional 42.4% sequence similarity. This is seemingly a high percentage of sequence conservation, but it does not guarantee that common epitopes will be available on the protein's surface to be recognized by neutralizing antibodies.

Figure 6:
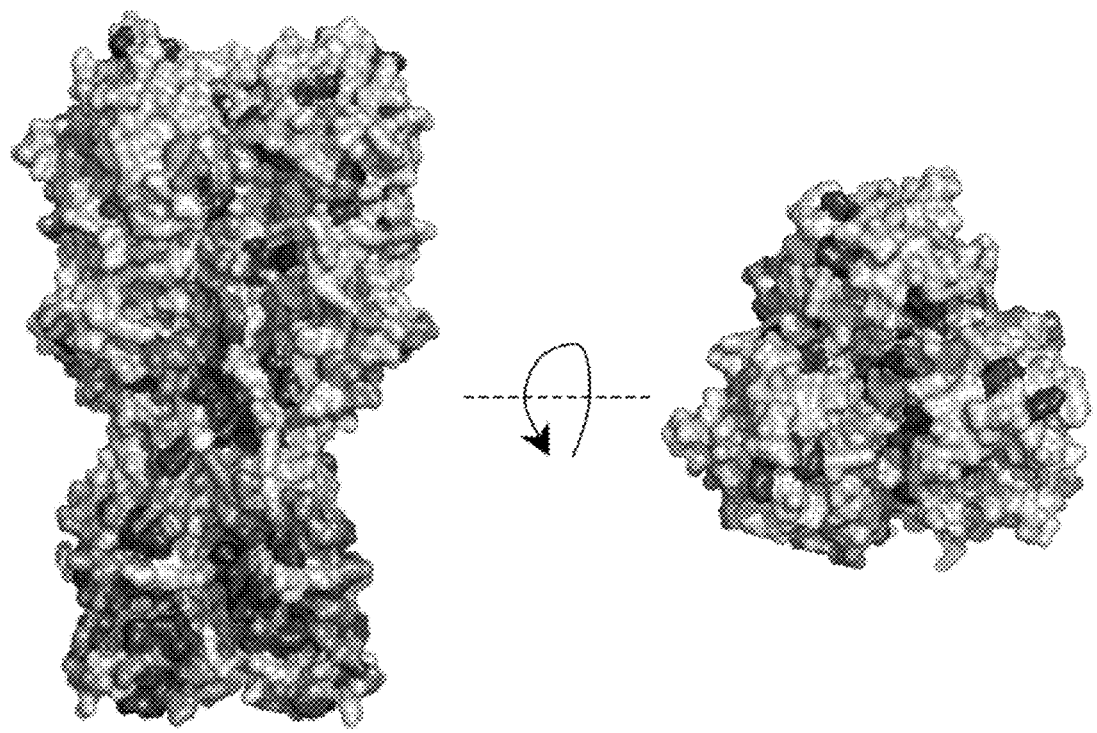

Therefore, structural information was obtained to supplement sequential analysis. To this end, the known structure of the H1N1 hemagglutinin from the 1918 influenza pandemic (Gamblin et al., "The Structure and Receptor Binding Properties of the 1918 Influenza Hemagglutinin," *Science* 303: 1838-1842 (2004), which is hereby incorporated by reference in its entirety) was used as an HA scaffold to three-dimensionally represent sequence homology (FIG. 6). The HA structure was colored to visually represent identity (black), similarity (dark gray), and divergence (light gray). The results of the alignment studies (FIG. 5) illustrate that a considerable extent of sequence similarity lies on the surface of hemagglutinin as accessible, potential epitopes. Thus, a certain degree of inter-isoform cross-reactivity can be expected for antisera, especially when subjects (human or otherwise) are vaccinated with recombinant, extraviral domains and not native, virus-anchored hemagglutinin. Additionally, the top-down view (FIG. 6) of the hemagglutinin active site reveals a highly dissimilar region of the protein between isoforms. Consequently, antibodies or small molecule inhibitors of the receptor binding site of one isoform are not likely to be broadly active against other hemagglutinins.

Hemagglutinin and neuraminidase polypeptides can be coupled to the array surface using any suitable chemistry for coupling polypeptides. Several different binding chemistries are described in the above-referenced U.S. Pat. No. 7,292,349 to Miller et al., which is hereby incorporated by reference in its entirety. A preferred approach, particularly for oxide coatings, involves the use of an aminoalkyl trialkoxysilane, followed by glutaraldehyde, which affords an amino-reactive surface capable of binding the hemagglutinin or neuraminidase polypeptides.

Binding of the hemagglutinin or neuraminidase polypeptides to each discrete location can be carried out manually or using an automated system. For manual arraying, polypeptide solutions can be arrayed in a volume of ~1 µL at a final concentration of 1-100 µg/mL, preferably 10-60 µg/mL, after a 1:1 dilution from a 2× stock (in modified phosphate-buffered saline ("MPBS")) into a solution containing 10% glycerol and 0.01% Tween-20. After incubating for 10 minutes in an ambient environment, the chips can be immersed in a solution of blocking buffer (1 mg/mL bovine serum albumin ("BSA") in Hepes buffered saline ("HBS")) for 45 minutes and then rinsed with MPBS buffer containing an additional 3 mM EDTA and 0.005% Tween-20 ("MPBS-ET"). For automated arraying, the polypeptide solutions can be arrayed by robotically printing using a Virtek ChipWriter Pro or comparable device at a final concentration of 1-100 µg/mL, preferably 40-60 µg/mL, after a 1:1 dilution from a 2× stock (in MPBS) into a solution containing 0.01-1% (v/v) 12-crown-4 ether in MPBS. After incubating for 60 minutes at 70° F. and 70% relative humidity in the microarray chamber, the chips can be immersed in a solution of blocking buffer (300 µg/mL BSA in HBS) for 60 minutes and then rinsed with MPBS-ET.

Once the array is prepared, the sensor chip can be exposed to serum samples obtained from individuals (or diluted serum samples), and then the presence (or absence) of one or more antibodies for a particular influenza strain can be determined based on the detection of a change (or lack of change) in the detector output following exposure of the sensor chip to the serum sample. As is well known in the art, the absence of a detectable signal does not necessarily mean that the antibodies are not present but rather that they are below detectable limits and, therefore, are not likely to be present. The image capture can be achieved by any of the detection systems described above, but preferably via an image array detector that captures an image of at least a substantial portion of the surface of the chip. For arrays of hundreds to hundreds of thousands of probes, an automated chip reader can be programmed to assess the change in reflectivity for each spot on an array based on the captured image.

As used herein, the individual from which serum samples are obtained can be any animal that is susceptible to infection by influenza, including humans and non-human primates, livestock, domesticated animals, and wild animals (particularly birds). Screening of livestock is particularly desired, because it is useful for monitoring the spread of influenza by wildlife. The serum sample can be obtained from both living individuals and a corpse post-mortem.

The arrays of the present invention are particularly useful for screening the efficacy of an influenza vaccine. Basically, the array is preferably used to screen pre- and post-immunization serum obtained from individuals to whom a vaccine has been administered. Following adequate time to allow for an immune response, post-immunization samples will be obtained and then screened against the array of the present invention. Dilution of the serum sample, typically from about 1:20 to about 1:2500, can be optimized based on the amount of hemagglutinin or neuraminidase loaded onto each discrete location of the array. Nevertheless, following exposure of the sample to the array, detection of antibody-hemagglutinin or antibody-neuraminidase reactivity can be assessed using the detection system of the system employed to read the sensor chip surface by AIR, SPR, BASI, ellipsometry, etc. A quantitative measurement of the immunoreactivity can be assessed.

If desired or required, sensitivity can be further enhanced by introduction of a secondary antibody, for example an antibody specific for IgG.

Further analysis can include, without limitation, ELISA, PCR, realtime-PCR, mass spectrometry, and liquid chromatography-NMR spectroscopy. Moreover, after detecting the presence of an antibody during use of the chip, the antibody itself can be dissociated from the hemagglutinin or neuraminidase polypeptide to which it was bound during use of the device. Dissociation can be achieved by any of a variety of ways including, without limitation, a glycine solution at low pH, a low pH water solution, a high pH water solution, a detergent solution (with low, moderate, or high concentrations), a low concentration denaturant solution (e.g., urea). After dissociation, the antibody (now free from the chip surface) can be recovered and then analyzed, if desired. Depending on the approach of subsequent down-stream analyses, it is possible to use the eluted samples directly or following one or more steps for concentration of the antibodies of interest.

Once the sensor chip is cleared of previously bound antibodies, the sensor chip can be re-used to screen other serum samples for the presence of anti-influenza antibodies.

EXAMPLES

The present invention may be further illustrated by reference to the following examples.

Materials and Methods for Example 1-3

Hemagglutinins

For the HA arrays, the following isoforms were used for manual and robotic arrays (isolated from humans unless specified otherwise): A/New Calcdonia/20/1999 (H1N1), A/Wyoming/3/2003 (H3N2), A/Hong Kong/56/1997 (H5N1), A/Hong Kong/213/2003 (H5N1), A/Vietnam/1203/2003 (H5N1), A/Teal/Hong Kong/W312/1997 (H6N1), A/Hong Kong/1073/1999 (H9N2). All HA's were purchased from Protein Sciences, Corp. (Meriden, Conn.) and/or provided by the research group of David Topham (University of Rochester, Rochester, N.Y.).

Human, Avian, and Mouse Samples

Human antisera to H5 vaccination were acquired from the University of Rochester Retrovirology Lab and Vaccine Evaluation Unit. The nine subjects studied were marked: 031, 033 (pre and post), 036, 037, 038, 064, 067, 069, and 071. The potential pathogenic states of the sera are unknown (i.e., information on tests for HIV 1/2, etc. are not known), and, as such, extreme caution was taken when handling the samples in a BSL-2 laboratory. Chicken antisera to avian influenza strains H5N9 and H7N3 were courteously donated by the Whittaker lab of the College of Veterinary Medicine at Cornell University. Negative control mouse plasma was obtained from the Pearce Laboratory at the University of Rochester Medical Center. Whole blood samples from five four-month old, female, 129Sv/J mice (original source Taconic, now bred in-house) were collected following an IP injection with pentobarbital and a heart right ventricle puncture. The blood was pooled over heparin and centrifuged to remove red blood cells.

Hemagglutinin Sequence Alignment

The complete amino acid sequences for all studied hemagglutinins were located through NCBI (Genbank) searches and conversion from the genomic nucleotide sequence (except H1N1, which was deposited as a peptide sequence). The Genbank accession numbers for each sequence, each of which is hereby incorporated by reference in its entirety, are as follows: ABW80979 (A/New Calcdonia/20/1999, H1N1) (Bragstad et al., "The Evolution of Human Influenza A Viruses from 1999 to 2006—A Complete Genome Study," *Virol J* 5:40 (2008), which is hereby incorporated by reference in its entirety), AY531033 (A/Wyoming/3/2003, H3N2) (Bragstad et al., "New Avian Influenza A Virus Subtype Combination H5N7 Identified in Danish Mallard Ducks," *Virus Res.* 109:181-190 (2005), which is herby incorporated by reference in its entirety), EF541403 (A/Vietnam/1203/2004, H5N1) (World Health Organization Global Influenza Program Surveillance Network, "Evolution of H5N1 Avian Influenza Viruses in Asia," *Emerg. Infect. Dis.* 11:1515-1521 (2005), which is hereby incorporated by reference in its entirety), AF250479 (A/Teal/Hong Kong/W312/1997, H6N1) (Hoffmann et al., "Characterization of the Influenza A Virus Gene Pool in Avian Species in Southern China: Was H6N1 a Derivative or a Precursor of H5N1?," *J. Virol.* 74:6309-6315 (2000), which is hereby incorporated by reference in its entirety), and NC_004908 (A/Hong Kong/1073/1999, H9N2) (Lin et al., Avian-to-Human Transmission of H9N2 Subtype Influenza A Viruses: Relationship Between H9N2 and H5N1 Human Isolates," *Proc. Natl. Acad. Sci. USA* 97:9654-9658 (2000), which is hereby incorporated by reference in its entirety). The primary structure alignment software Multalin (v5.4.1) (Corpet, F., "Multiple Sequence Alignment with Hierarchial Clustering," *Nucl Acids Res* 16:10881-10890 (1988); Combet et al., "NPS@: Network Protein Sequence Analysis," *Trends Biochem Sci.* 25:147-150 (2000), which are hereby incorporated by reference in their entirety) was used to align each HA sequence of approximately 560-570 amino acids. Multalin parameters were set to use the identity symbol comparison table and the identity scoring method. The upper and lower limits of sequence conservation were set to 100% and 50%, respectively. The alignment output is shown in FIG. 5.

For graphical representation, the sequence of the solved hemagglutinin structure H1N1 (Combet et al., "NPS@: Network Protein Sequence Analysis," *Trends Biochem Sci.* 25:147-150 (2000), which is hereby incorporated by reference in its entirety) (PDB ID: 1RUZ) was used as a scaffold and rendered using MacPYMOL (DeLano, W. L., *The PyMOL Molecular Graphics System*, DeLano Scientific, Palo Alto, Calif., USA (2002), which is hereby incorporated by reference in its entirety). Its sequence was added to the Multalin alignment algorithm in order to verify the position of each conserved/similar amino acid residue; in MacPYMOL, each residue that was 100% conserved was colored 'black', 50%-99% conserved was colored 'dark gray', and <50% conserved was colored 'light gray'. The hemagglutinin homology structure was then ray traced in order to display the 'spike' (side on) and 'active site' (top down) orientations (see FIG. 6).

Manual Hemagglutinin Array Experiments

AIR substrates were prepared to a starting $SiO_2$ thickness of 1381 Å and functionalized using PITC general amine attachment chemistry. The HAs used for manual array experiments were H1N1, H3N2, all three H5N1s, and H6N1. HAs were manually arrayed in a volume of 1 µL at a final concentration of 20 µg/mL after a 1:1 dilution from a 2× stock (in MPBS) into a solution containing 10% glycerol and 0.01% Tween-20. Human IgG (positive control) and fluorescein antibodies were arrayed at a final concentration of 50 µg/mL in the same volume and buffer dilution. Probe solutions were allowed to incubate for 10 minutes in an ambient environment, after which the chips were immediately immersed in a solution of blocking buffer (1 mg/mL BSA in HBS) for 45 minutes. The chips were then rinsed with MPBS-ET, and 150 µL of 100% human serum samples were pipetted onto the surface (some variable sample dilution will have occurred). After a 45 minute incubation period, the chips were rinsed with MPBS-ET and added to a shaking bath of MPBS-ET for 5 minutes. The chips were then rinsed with ddH2O, dried under nitrogen, and imaged on a G3 reflectometer. Reflectance values for each spot were compared to the reciprocal spot on a negative control chip (MPBS-ET only) and normalized to the α-fluorescein negative control.

Microarrayed Hemagglutinin Experiments

AIR substrates were prepared to a starting $SiO_2$ thickness of 1393 Å and functionalized using glutaraldehyde general amine attachment chemistry. The difference between the oxide thicknesses required for macro- and microarrayed HA assays are presumably caused by the slight broadening of the AIR reflectance minimum due to the inefficient coupling of reflected light to the G4 reflectometer detector. All probe spots were printed in eight replicates. The HAs used for manual array experiments were H1N1, H3N2, H5N1 (Vietnam/1203/2003), H6N1, and H9N2 (human antiserum experiments only). HAs were robotically printed using a Virtek ChipWriter Pro at a final concentration of 40 µg/mL (50 µg/mL for H9N2) after a 1:1 dilution from a 2× stock (in MPBS) into a solution containing 0.1% 12-crown-4 in MPBS. Human IgG and human IgM antibodies (positive controls) were arrayed at 100 µg/mL. Human serum albumin (HSA) and α-fluorescein (negative controls) were arrayed at final concentrations of 200 µg/mL and 10 µg/mL, respectively, in the same buffer dilution. Probe solutions were allowed to incubate for 60 minutes at 70° F. and 70% relative humidity in the microarray chamber. Afterwards, the chips were immediately immersed in a solution of blocking buffer (300 µg/mL BSA in HBS) for 60 minutes. The chips were then rinsed with MPBS-ET, and 50 µL of human serum samples were pipetted onto the surface (some variable sample dilution will have occurred). After a 60 minute incubation period, the chips were rinsed with MPBS-ET and added to a shaking bath of MPBS-ET for 5 minutes. The chips were then rinsed with ddH$_2$O, dried under nitrogen, and imaged on a G4 reflectometer. Reflectance values for each spot were compared to the reciprocal spot on a negative control chip (MPBS-ET only) and normalized to HSA negative control.

For chicken H5N9 and H7N3 antiserum experiments, all methods were kept the same except for the exclusion of H9N2 as a probe (lack of availability), removal of HSA as a negative control, removal of α-IgM as a positive control, and the exchange of α-IgY for α-IgG as a positive control. Also, recombinant green fluorescent protein (rGFP) was arrayed as a secondary control at a concentration of 50 µg/mL. In the presence of chicken antiserum, rGFP served as an additional negative control; at low antiserum dilutions, α-rGFP was supplemented at a concentration of 5 µg/mL as a positive spike control.

Example 1

Manually Prepared Hemagglutinin Arrays

Initial experiments utilizing manually arrayed hemagglutinins at high concentrations were performed to study both the arrayability of these proteins and the proper starting chip thickness. At 100 µg/mL of A/Vietnam/1203/2004 (H5N1), an oxide of 1360 Å was determined to be the ideal film thickness to give suitable unbound probe intensities. While these spots were resolvable, an early experimental concern lay in the general amine attachment chemistry: HAs are homotrimeric and contain roughly 30 solvent accessible amines per monomer. The orientation of the immobilized molecule, therefore, will be completely random. The oligomeric state may ensure that there is a solvent accessible face available to bind to specific antibodies, but orientations that result in an effectively inactive sensor are also possible.

Attempts to observe signal changes upon the addition of an antibody specific to the A/Vietnam/1203/2004 (H5N1) hemagglutinin (enzyme product number IA-005-01000) failed at these high HA concentrations presumably due to steric crowding at the surface that impeded epitope recognition by large antibodies. Ideally, since each HA isoform is identical in size—differing only slightly in sequence—the solution concentrations used to array each should also be identical. The A/New Calcdonia/20/1999 (H1N1) isoform was supplied at the lowest stock concentration of 66 µg/mL, and, thus, was the limiting probe for this study; all probe molecules were diluted such that they could be supplemented with a sufficient amount of stabilization solution consisting of glycerol and Tween-20. Due to this, subsequent experiments were performed using 20 µg/mL as a final concentration for all HAs. This low concentration, and a subtle alteration to the washing protocol during the surface derivitization, caused the new optimum chip starting thickness to increase to 1381 Å. A test array was created and consisted of the aforementioned H1N1 and H5N1 experimental hemagglutinin probe spots, as well as positive and negative control spots of α-IgG and α-fluorescein, respectively. These arrays were screened against a specific A/New Calcdonia/20/1999 (H1N1) antibody (Fitzgerald product number M32210) as well as the H5N1 antibody. An interesting result of these experiments was that the H1N1 antibody seemed to preferentially recognize the H5N1 isoform, while the H5N1 antibody only moderately recognized both HAs. This was not completely unforeseen, though, since antiserum cross-reactivity was predicted by sequence homology.

Figure 7:
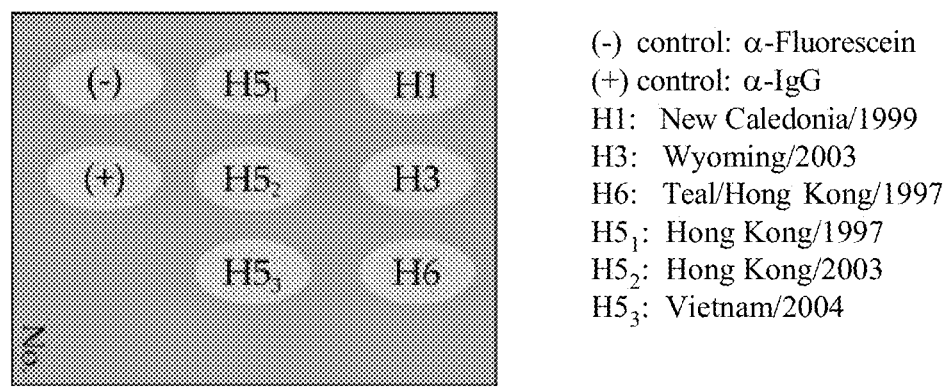

A full HA array, containing six isoforms and a positive and negative control, was manually generated in preparation for a small-scale clinical trial (FIG. 7). Antisera were obtained from six different subjects: five were inoculated with various amounts of A/Hong Kong/156/1997 (H5N1) on two separate visits, and one subject was given a placebo injection only (see Table 1). All tests were performed blind.

TABLE 1

Tabulated Results from Traditional Vaccination Efficacy Tests for Each Subject Inoculated with Varying Amounts of Antigen

| Subject No. | Amount (μg) | ELISA OD | Western Blot | Neut. Titer | HAI, 1 Titer | HAI, 3 Titer |
|---|---|---|---|---|---|---|
| 056 | 90/90 | 1.748 | positive | 453 | 2,560 | 20 |
| 068 | 90/10 | 0.652 | negative | 14 | 320 | 10 |
| 076 | 25/25 | 1.677 | negative | 20 | n/p | n/p |
| 079 | placebo | 0.235 | negative | 10 | n/p | n/p |
| 080 | 25/25 | 1.856 | positive | 80 | n/p | n/p |
| 081 | 90/60 | 1.160 | negative | 14 | 160 | 20 | n/p = experiment not performed

Figure 8A:
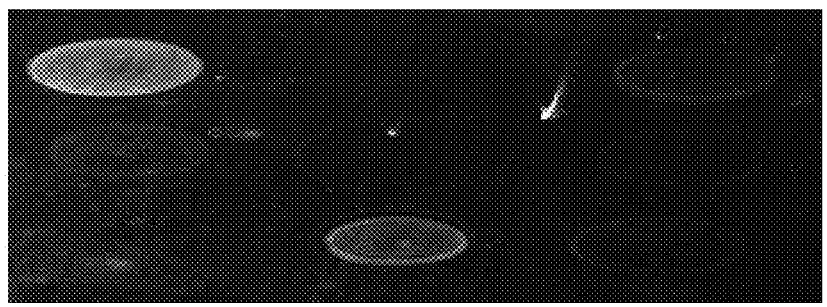
Figure 8B:
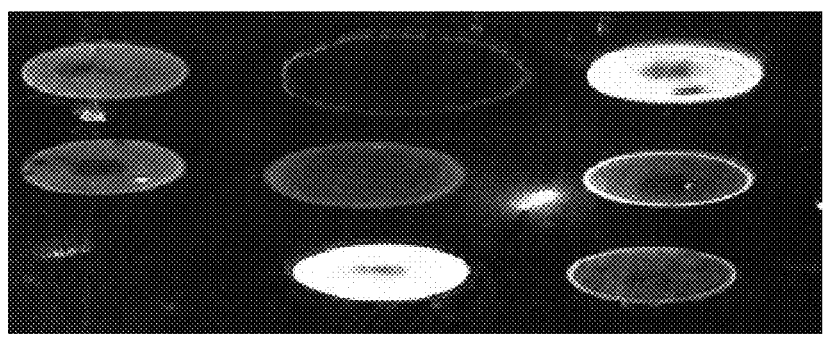
Figure 9:
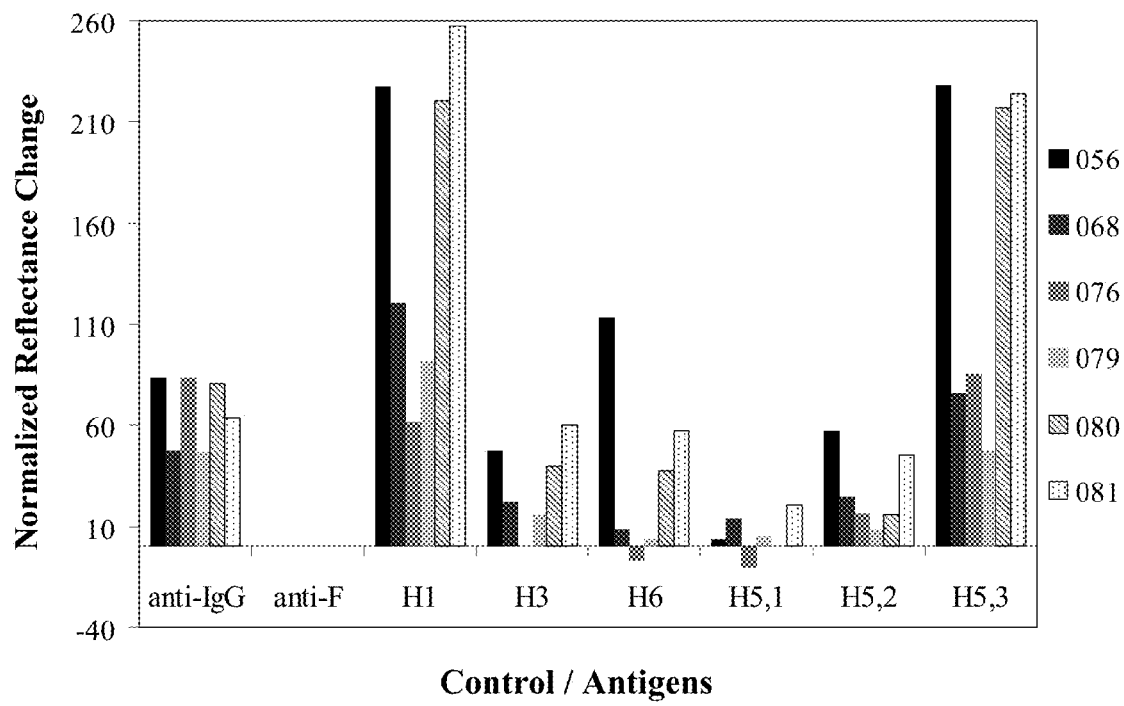

Aliquots of undiluted serum were utilized on a full HA array by AIR using a detection system of the type described in U.S. patent application Ser. No. 10/282,274 to Miller et al., filed Oct. 28, 2002, now U.S. Pat. No. 7,292,349, issued Nov. 6, 2007, which is hereby incorporated by reference in its entirety. Representative pre-exposure and post-exposure images are shown in FIG. 8A-B, while the full quantification of reflectance changes from all chips is shown in FIG. 9.

It is important to make known that these studies were performed blind, with no prior knowledge of the amount of antigen each subject was inoculated with, the results of antiserum response as monitored by traditional means, or the identity of the placebo sample. Traditional assays ELISA, western blot against antiserum, viral neutralization, and hemagglutinin inhibition (HAI)—were performed on sera collected from the subjects seven days after their second immunization. These results are shown in Table 1.

A few traits are immediately apparent from the clinical antiserum data that corroborate the studies with purified antibodies. Firstly, there is a high degree of correlation between the responses to the New Calcdonia/20/1999 and Vietnam/1203/2004 hemagglutinins. Secondly, there is limited response from the Hong Kong/156/1997 spot regardless of subject. Thirdly, specific antisera appear to have elicited a higher response to general HA epitopes than others. It is peculiar, however, that very little response is seen at the Hong Kong/156/1997 spot, because this was the recombinant isoform that was used to inoculate the patient population. However, while this isotype has confirmed activity in T-cell assays, it is unlikely to exist in a native, folded conformation. In addition, the reflectance changes that occur are specific to the HA probes since the α-fluorescein control spot intensity changes were negligible for all assays (average value of 5.4 units). This is an exceptional result considering the experiments utilized undiluted antiserum.

Figure 10:
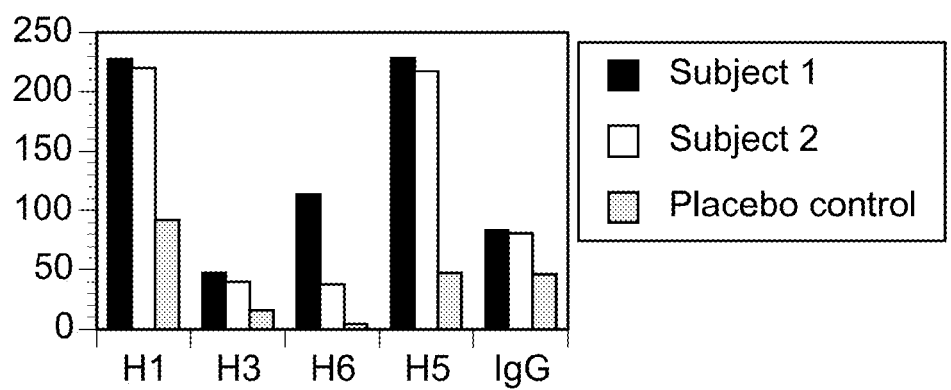
FIG. 10 is graph illustrating the comparative analysis of AIR data for subject samples whose ELISA and western blot results corroborated. Subject 1 is subject 056; Subject 2 is subject 080; the placebo control is subject 079. The H5 hemagglutinin is H5,3 (Vietnam/1203/2004).

Comparing the AIR results with the conventional analyses shown in Table 1, a high degree of similarity is observed. Samples from subjects 056 and 080 show a high AIR reflectance (FIGS. 9 and 10), ELISA OD, a good neutralization titer, and a positive western blot. Subject 056 shows a high New Calcdonia/20/1999 cross-reactivity (FIG. 9). Subject 068 had high HA cross-reactivity as seen by AIR and HA1 titers (FIG. 9). An important facet of the blind study was to determine whether the placebo subject could be resolved by AIR. Based on the AIR results, the three candidates for the placebo sample were Subjects 068, 076, and 079. Subject 068 was identified due to low responses, aside from New Calcdonia/20/1999 and Vietnam/1203/2004 HAs. Subject 076 was identified because this sample generated one of the lowest two overall reactivities. Subject 079 was also identified due to low activity across all H5 hemagglutinin spots. Indeed, the identity of the placebo sample was later disseminated to be from subject 079.

The low reactivity for subject 068 may be explained by the smaller second inoculation dosage that could have led to a decrease in the secondary immune response and, therefore, a lesser amount of antibody generation. The results from subject 076 are more difficult to explain. It is possible that the ELISA OD is misleading and this subject had a very weak immune response to vaccination, or the immunogenic HA epitope for this subject is not available when the Hong Kong/156/1997 hemagglutinin is surface-immobilized. One dissimilarity, however, was subject 081. By traditional methods, subject 081 appeared to be a poor candidate for successful vaccination because their antiserum neutralization titer was low and the western blot was negative, but by AIR subject 081 garnered some of the highest responses across the array. There is the potential, however, that by tethering these HAs to the substrate surface that certain epitopes are preferentially exposed or obscured. The reflectance values observed, therefore, would be distorted with respect to solution-based, or matrix-based, assays.

Importantly, these results—obtained using a label-free, "reagentless" technique in less than 30 minutes—were entirely consistent with those derived via a comparative ELISA assay.

Example 2

Viral Surveillance in Avian Flocks

Avian-to-human contact is the main route of H5N1 influenza virus transmission (Sandrock et al., "Clinical Review: Update of Avian Influenza A Infections in Humans," *Crit. Care* 11:209 (2007), which is hereby incorporated by reference in its entirety). Therefore, the ability to monitor global poultry populations is critical for protecting human health. Moreover, surveillance is of agricultural and humane concerns as well: as of the end of 2006, over 240 million poultry have been preventatively destroyed to stem the spread of the avian influenza virus (World Organization for Animal Health, *Avian influenza: Fact Sheet*, accessed Apr. 16, 2008, which is hereby incorporated by reference in its entirety).

Samples of chicken H5N9 and H7N3 antisera were obtained from the Whittaker lab at the College of Veterinary Medicine, Cornell University. The H5N9 antiserum would serve as a substitution for avian H5N1, while the H7N3 virus has also shown the potential to be infectious to humans (Tweed et al., "Human Illness from Avian Influenza H7N3, British Columbia," *Emerg. Infect. Dis.* 10:2196-2199 (2004), which is hereby incorporated by reference in its entirety). In addition, avian antiserum experiments would serve as an excellent model system to study concurrently with a modification of AIR methodology. These experiments were performed with robotically printed arrays as described above.

Figure 11:
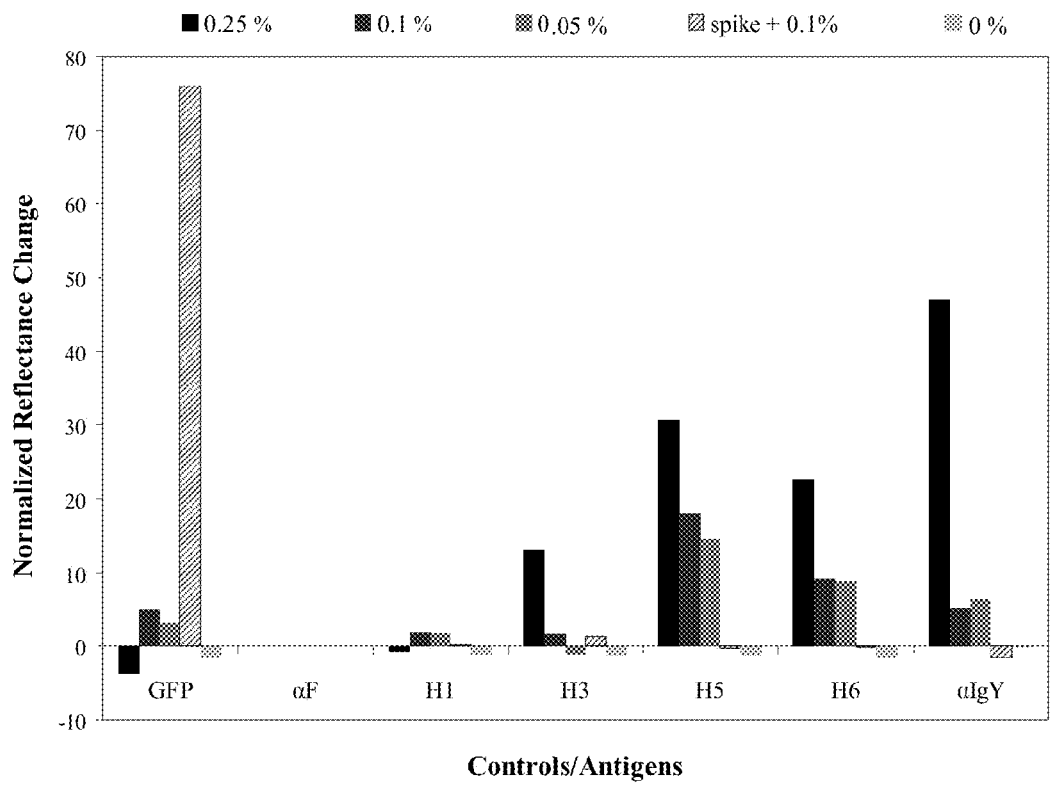
FIG. 11 is a graph illustrating H5N9 avian antiserum titration results. All reflectance changes are normalized to changes in the α-fluorescein negative control spot. Recombinant GFP served as a secondary negative control and a supplementary positive spike control An IgY antibody acted as the experimental positive control. A second set of chips exposed to buffer alone was the 0.0% control assay.

For the avian antiserum experiments, arrays containing New Calcdonia/20/1999 (H1N1), Wyoming/3/2003 (H3N2), Vietnam/1203/2004 (H5N1), and Teal/Hong Kong/W312/1997 (H6N1) were created. To these arrays, an α-IgY positive control, and α-fluorescein and recombinant green fluorescent protein (rGFP) negative controls were added. The rGFP spot would simultaneously serve as a positive spike control for dilute solutions. Unfortunately, the H5N9 antiserum was supplied in a limited volume and only a preliminary titer could be acquired, shown in FIG. 11. A fairly large reflectance increase was observed for H3, H5, and H6 at higher concentrations of antiserum. H3 appeared to be less specific since it did not titrate well as dilutions were introduced, while H5 and H6 changes corresponded well to concentration changes. The H1 hemagglutinin showed negligible reflectance changes for all screened concentrations. The IgY antibody appeared to be less active than anticipated, given the large serum immunoglobulin concentration; for example, when the array was supplemented with an additional column of α-human IgG, the human immunoglobulin-specific antibody displayed a greater sensitivity than the antibody for chicken immunoglobulin (in the context of H7N3 antiserum experiments). Recombinant GFP showed little non-specific adsorption towards the chicken antiserum, but was 'active' in that it was readily recognized by an addition of α-GFP to a dilute antiserum solution. A 50% H5N9 antiserum dilution was also performed on a set of chips, but nonspecific binding to the surface precluded repeatable quantification of binding.

Figure 12:
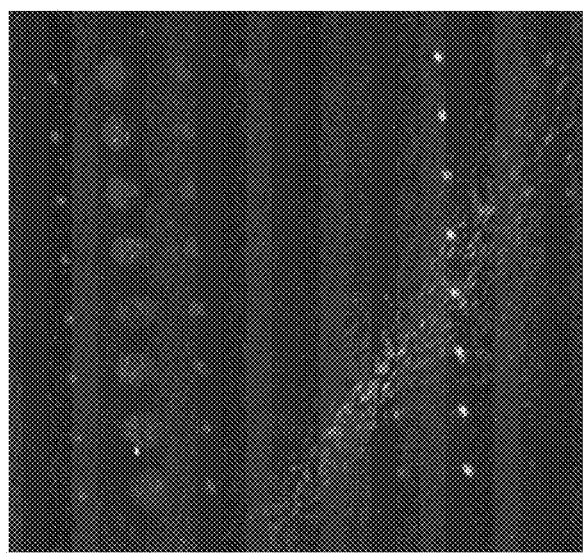
FIG. 12 is an AIR image of an HA microarray for H7N3 antiserum experiments. The chip was exposed to a 10% solution of H7N3 antiserum. Each probe type is printed eight times in a column. From left to right, probe molecules are: H1, H3, H5, H6, blank, α-IgY, α-IgG, and α-fluorescein. Note that α-fluorescein negative control is not easily visible, and that α-IgY is barely active at this concentration of antiserum.
Figure 13:
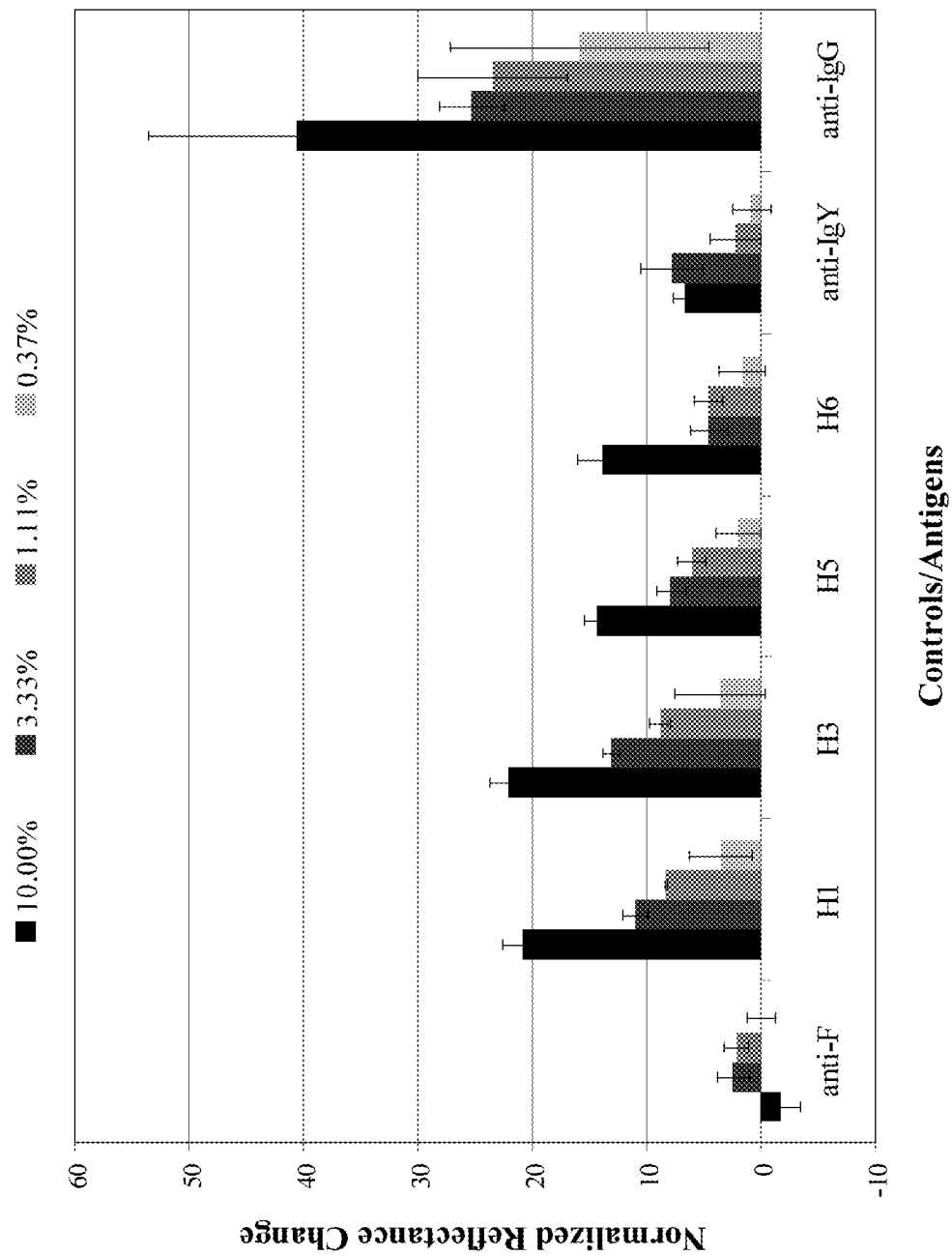
FIG. 13 is a graph illustrating H7N3 avian antiserum titration results performed as sequential $\log_3$ dilutions. All changes were normalized to the α-fluorescein control spot. Each concentration was repeated three times.

While the H5N9 antiserum was quickly depleted, at the very least it afforded a titration window in which to effectively study H7N3 antiserum activity. For these experiments, the dilution window was focused to range from 10% to 0.37% (three $\log_3$ dilutions). Handling more dilute antiserum concentrations allowed for conservation and for a larger amount of replicate experiments to be performed. FIG. 12 shows an image of a hemagglutinin microarray imaged on the G4 AIR reflectometer after exposure to 10% H7N3 antiserum. The spot morphologies are typical of each probe type. The large flare in the bottom right corner of the image is scatter caused by particulates on the reflectometer's imaging system. This variety of reflectivity abnormality is easily circumvented during image processing. The results of the H7N3 antiserum titration was quite different than that of the H5N9 antiserum, as a large H3 cross-reactivity was observed (FIG. 13). Unfortunately, a recombinant H7N3 hemagglutinin is not commercially available and therefore unable to be implemented into this array. Modest reflectance increases were observed for all arrayed hemagglutinins, and all HA signals titrate well with reducing antiserum concentration. The sensitivity of AIR is clearly demonstrated by the statistically distinct reflectance changes for substrates exposed to 10% antiserum versus 3.33% antiserum. The standard deviations in the average observed signal change are large for the more dilute solutions, but this can be accounted for by the systematic errors stemming from additional sample dilution caused by introducing target solutions to wet chips.

As expected, stark differences were observed between H5N9 and H7N3 avian antisera. Comparison of a single high antiserum dilution (as performed for the human antisera described below) establishes trends in cross-reactivities between arrayed HAs: H5N9 antiserum is specific for H5 and, to a lesser extent, H6, while displaying no reactivity towards either H1 or H3 hemagglutinins; H7N3 antiserum, on the other hand, exhibits reactivity over the entire hemagglutinin panel, with a slight specificity for H1 and H3. These results serve to prepare for more extensive avian surveillance studies to be performed in the future with the inclusion of a larger HA array and more diverse poultry population.

Example 3

Larger Hemagglutinin Arrays

Arrays were prepared with the automated microarray printer using five hemagglutinin isoforms as follows: H1=A/New Caledonia/20/1999 (H1N1); H3=A/Wyoming/3/2003 (H3N2); H5=A/Vietnam/1203/2004 (H5N1); H6=A/Teal/Hong Kong/W312/1997 (H6N1); and H9=A/Hong Kong/1073/1999 (H9N2). Several controls were also included on the array, including human serum albumin (HSA) as the "normalizing" negative control, and anti-fluorescein as a secondary negative control element. Antibodies to human IgG and human IgM serve as positive controls.

Figure 14:
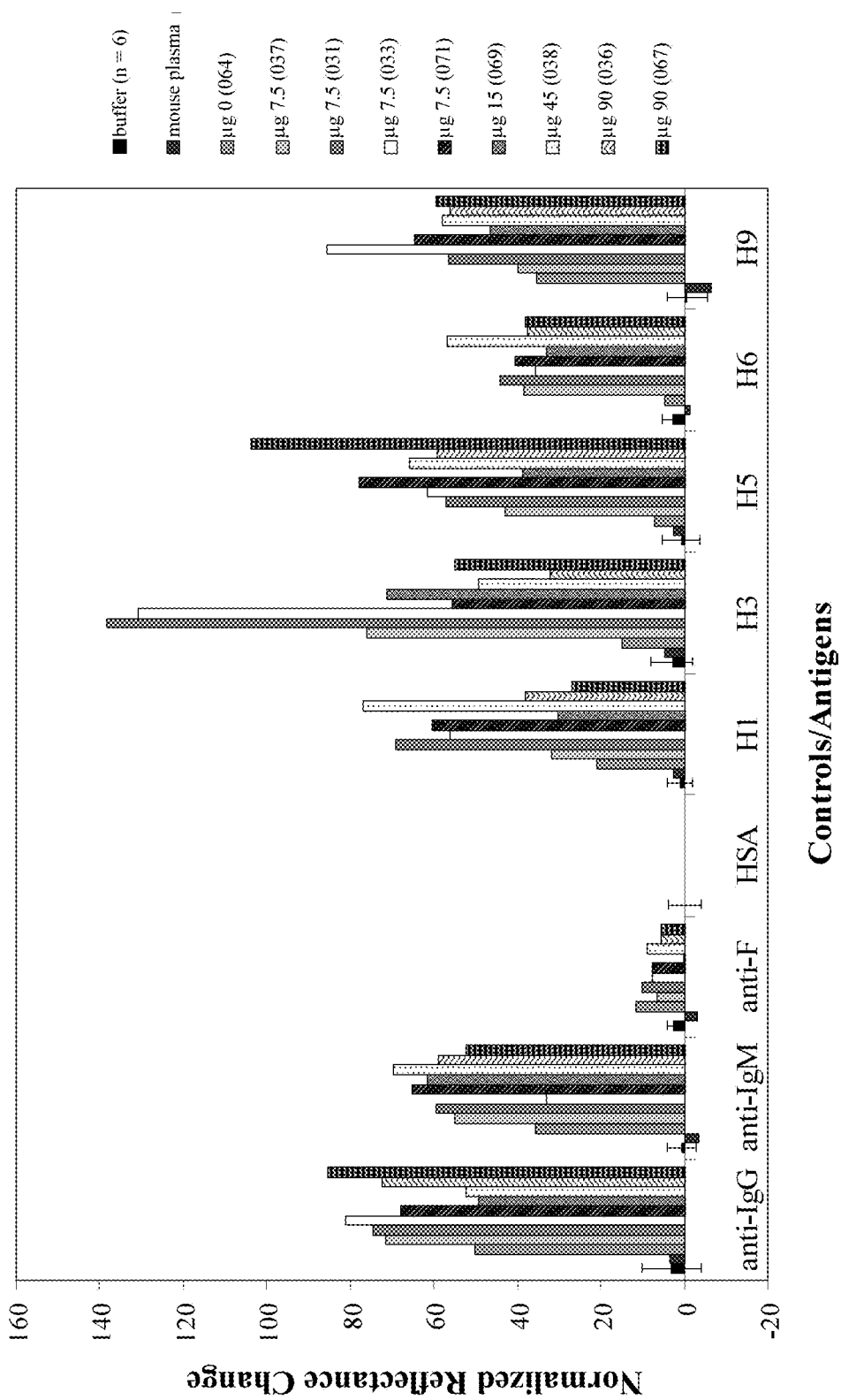
FIG. 14 is a graph showing the results for subject antisera screened at a 5% dilution. The "buffer" column corresponds to the average and standard deviation of the MPBS-ET control chips from six experiments. The HA array responses are labeled according to subject number and dose of H5 received (in micrograms).
Figures 17A, 17B:
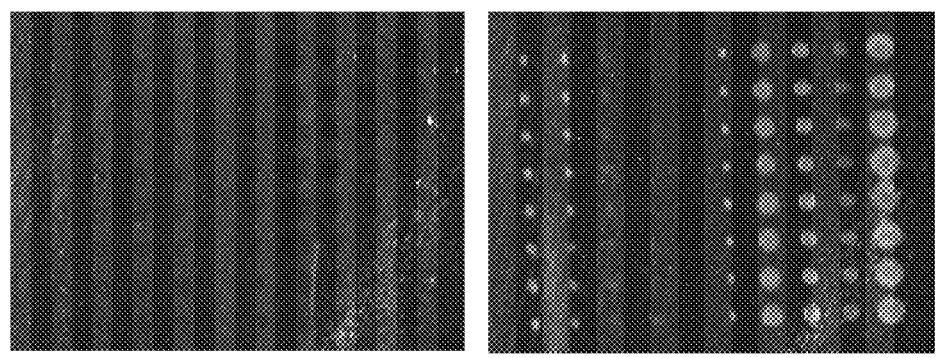
FIGS. 17A-B show robotically printed HA microarray for human antiserum experiments. A background image (FIG. 17A) and an image of an experimental array exposed to 5% antiserum (FIG. 17B; subject 071) are depicted. From left to right, spot identities are α-IgG, α-IgM, α-fluorescein, HSA, blank, H1, H3, H5, H6, and H9.
Figure 18:
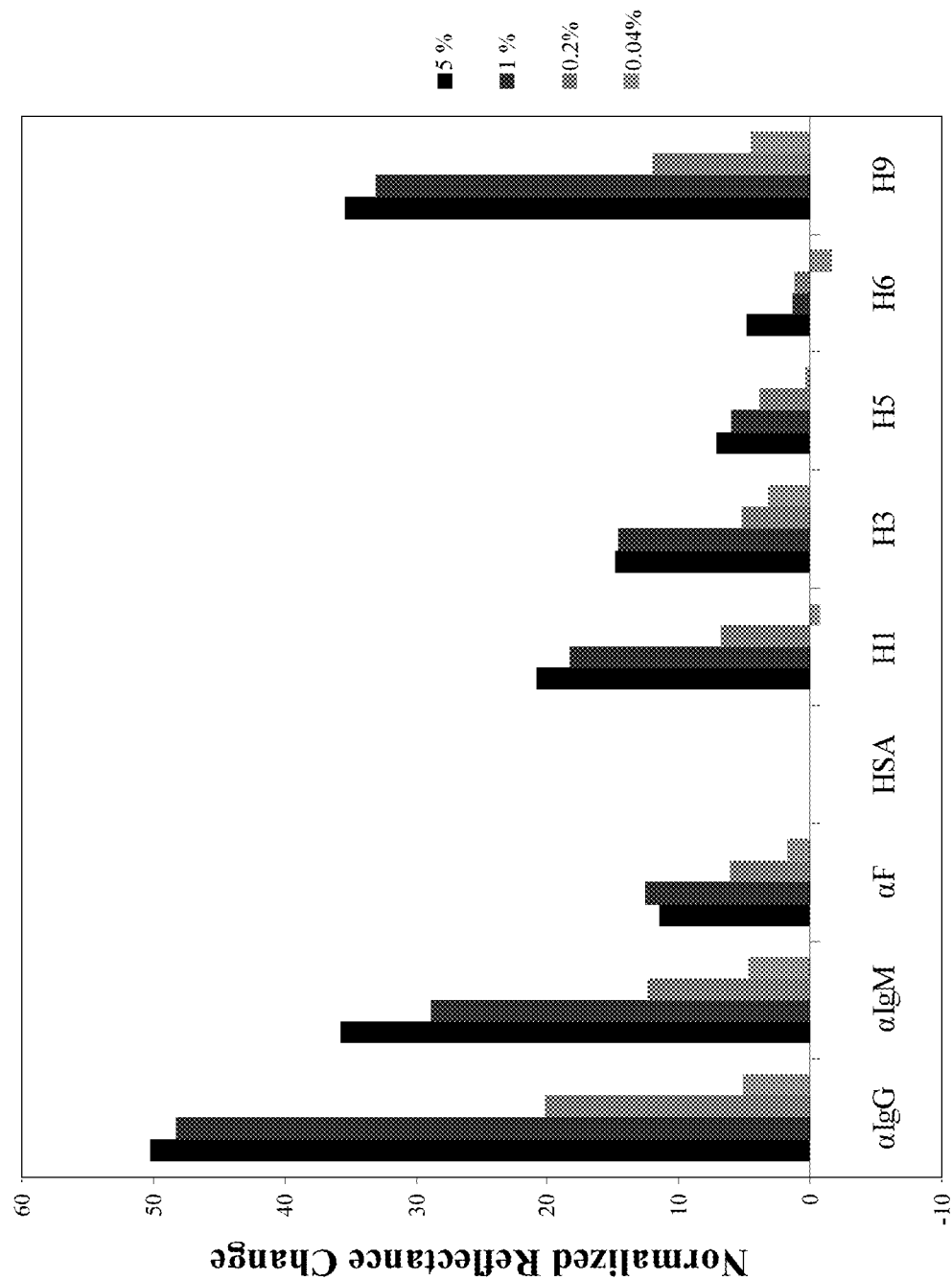
FIG. 18 shows an antiserum titration for placebo subject 064.

While the preliminary human antiserum results were successful in proving that AIR data could augment the results of traditional vaccination assays, there were two major limitations that could not be overcome by conventional manual arraying techniques: expanding the array to include an increased probe redundancy and removing the "human variable" by robotically controlling the volume and morphology of printed arrays. As was demonstrated with the avian antiserum experiments of the preceding section, utilizing a robotic microarrayer solves both technique inadequacies in a controlled and repeatable manner. Additionally, the A/Hong Kong/1073/1999 (H9N2) hemagglutinin was supplemented into the full array, along with two more control probes: an antibody to human IgM would serve as a second positive control (Lacroix-Desmazes et al., "Analysis of Antibody Reactivities Toward Self Antigens of IgM of Patients with Waldenstrom's Macroglobulinemia," Int Immunol 9:1175-1183 (1997), which is hereby incorporated by reference in its entirety), and human serum albumin, through solution-phase competition effects, would be an effective additional negative control (FIG. 14). FIG. 17B shows a representative image of a hemagglutinin microarray imaged on the G4 AIR reflectometer after exposure to 5% antiserum of subject 071.

From assays performed on serum from a randomly selected subject from the clinical population, the effective experimental titration range for the human antiserum experiments was determined to be between 5% (1:20 dilution) and 0.04% (1:2500 dilution). 5% antiserum was dilute enough to negate signals from non-specific binding while retaining a large, non-saturating reflectance increase, and 0.04% (a 1:2,500 dilution) was dilute enough to, in effect, titrate out reflectance changes to zero for most samples. This dilution series was performed in $\log_5$ steps for all titrated samples. The majority of the antisera, however, were studied at a 5% dilution alone to quantify trends in cross-reactivity and to identify potential placebo subjects. Based on low H5 reflectance changes at the upper 5% titer, samples from 06FRO037 and 06FRO069 are likely recipients of placebo (FIG. 14). Also, the buffer controls arrays for antiserum experiments (N=6) were analyzed to quantify array-to-array reproducibility. The largest reflectance variations between control chips were observed for α-IgG spots (3.05+/−8.1), while the most reproducible spots were α-fluorescein (2.66+/−1.8). The "noise" of the assay is then approximately 3 units, and, therefore, reflectance changes in this range are considered negligible.

Figure 15:
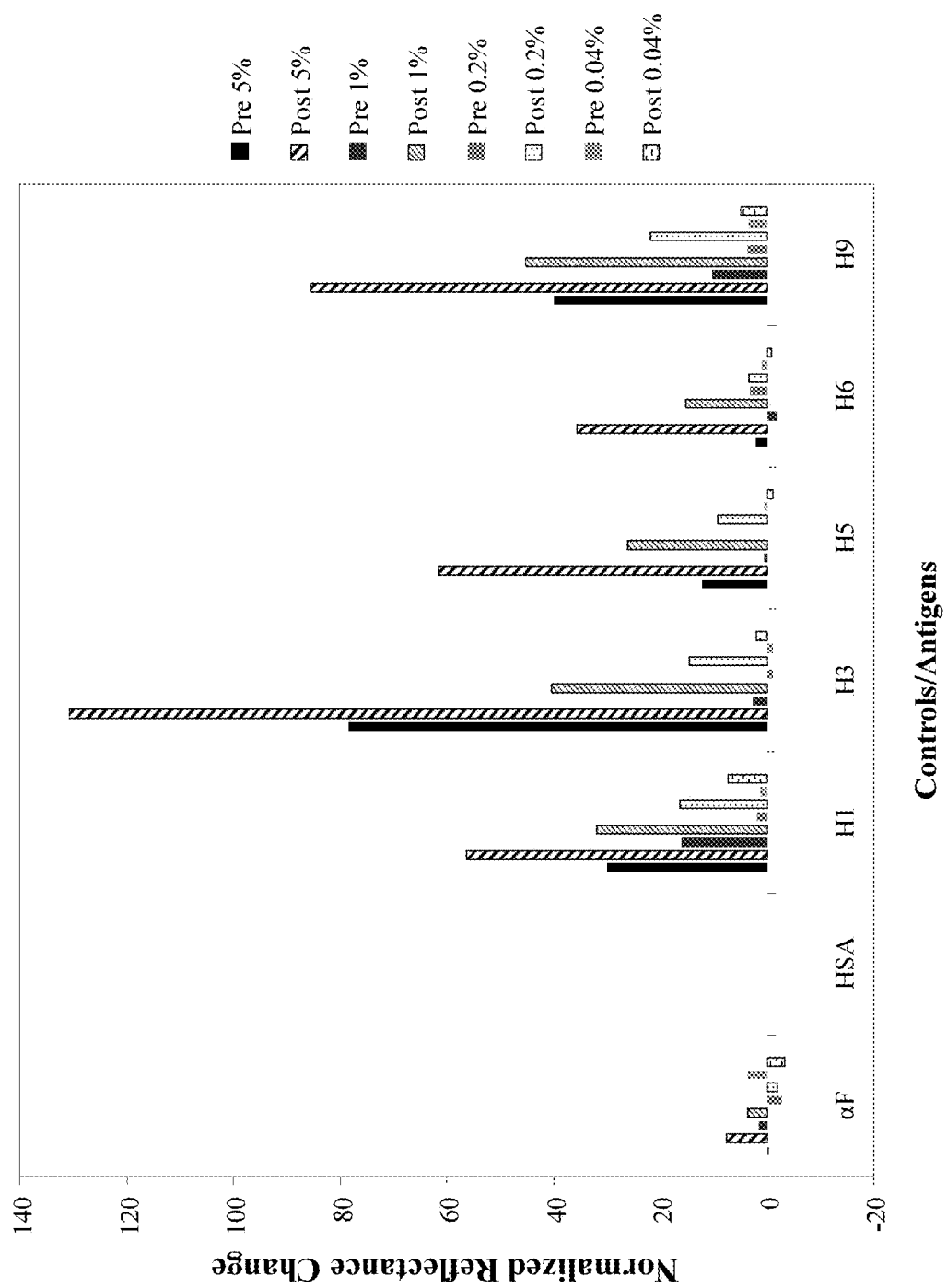
FIG. 15 is a graph showing a comparison of pre- and post-inoculation reflectance changes for subject 06FRO033 for $\log_5$ antiserum dilutions from 5% to 0.04%.
Figure 16:
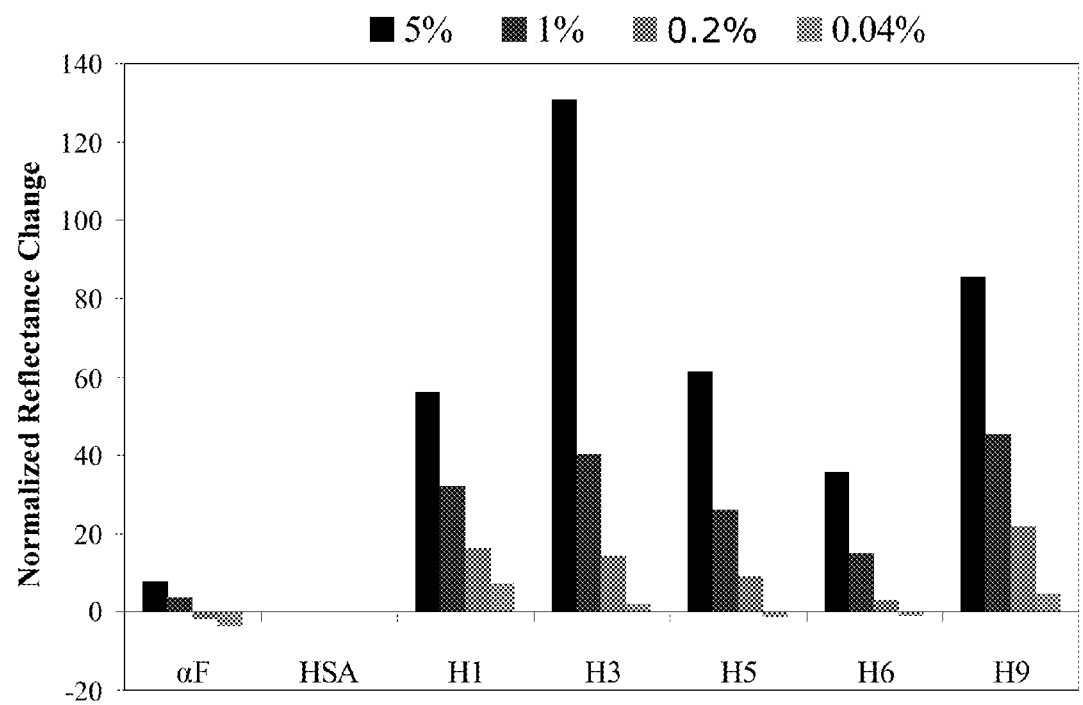
FIG. 16 is a graph illustrating the results of subject 06FRO033 antiserum titrations from 5% to 0.04%.

One subject also had pre-inoculation sera aliquoted to quantify innate resistance and determine the actual protective effect of the H5 inoculation. Reflectance changes derived from subject 06FRO033 indicated modest responses to H3 hemagglutinin, potentially due to memory immunity derived from a prior influenza infection, and slight cross-reactivities to H1 and H9 hemagglutinins (FIG. 15). However, only basal recognition of H5 and H6 hemagglutinins were observed in the pre-inoculation antiserum aliquot, and, since these interactions were not titratable over the concentration range of the experiment, they were presumably not specific to those isoforms. Nevertheless, upon inoculation with H5, subject 06FRO033 gained considerable specific protective effects against H5 and all HAs in the array (FIG. 16). Moreover, since these interactions titrated well over the screened concentrations-four $\log_5$ serial dilutions (5%, 1%, 0.2%, and 0.04%), they are assuredly a consequent of specific immunological responses. As expected, there was a dose-dependent change in signal over the course of dilutions. The sensitivity of AIR is clearly demonstrated by the statistically distinct reflectance changes for substrates exposed to as little as 0.2% antisera.

The placebo sample was identified as being derived from subject 064, which is clearly observed in the reflectance data displayed in FIG. 14. A full antiserum titration was then performed in order to monitor the rate of signal depletion against the HAs. Similar to what was observed with the pre-inoculation sample of subject 033, there is very little basal recognition of H5 and H6 in the non-vaccinated population; however, antibodies to H1, H3, and H9 hemagglutinins are present in normal human serum. This is shown in FIG. 18.

Through the National Institutes of Health, John Treanor (University of Rochester, Rochester, N.Y.) provided H5 hemagglutinin inhibition data for all subjects screened by AIR (Table 2). With the exception of subjects 036 and 067, there appears to be little correlation between the amount of H5 used to inoculate a subject and their ability to generate inhibitory antisera as observed through the H5 HA1 titer. Interestingly, subjects 031 and 036 had higher HAI titers six months subsequent to the conclusion of the study than those detected during the course of vaccination (post-vaccination visits 1 and 2 in Table 2). AIR results, however, were less discriminating. There are definite discrepancies between dosage, HAI titer (post-vaccination visit 2), and AIR reflectance change as typified by the results from samples derived from subjects 036, 067, and 071. This is expected, though, since all antibodies generated for hemagglutinin-specific epitopes have the potential to cause reflectance increases, and not just those that inhibit activity. However, it is not possible to conclude that the HA arrays, as monitored by AIR, are clearly capable of discerning pre- and post-inoculation antisera and samples derived from placebo and experimental subjects. Moreover, these results are consistent with what would be expected from similarly performed ELISA and western blot experiments, with respect to agreement with HAI titers and inoculation dosage, while vastly increasing the amount of data that can be acquired from a single subject-derived sample.

TABLE 2

Comparison of H5 Hemagglutinin Inhibition Titers Performed at Various Stages Along the Clinical Study

| Subject | Dose (μg) | HAI post-vac 1 | HAI post-vac 2 | HAI 6 months | AIR Result |
|---|---|---|---|---|---|
| 064 | 0 | 5.0 | 5.0 | 5.0 | 7.11 |
| 037 | 7.5 | 5.0 | 5.0 | 5.0 | 42.78 |
| 031 | 7.5 | 5.0 | 5.0 | 10.0 | 56.94 |
| 033 | 7.5 | 5.0 | 7.1 | 5.0 | 61.57 |
| 071 | 7.5 | 5.0 | 5.0 | 5.0 | 77.87 |
| 069 | 15 | 5.0 | 5.0 | 5.0 | 38.81 |
| 038 | 45 | 5.0 | 5.0 | 5.0 | 65.83 |
| 036 | 90 | 28.3 | 28.3 | 56.6 | 59.28 |
| 067 | 90 | 5.0 | 160.0 | 5.0 | 103.75 |

AIR data acquired at a 5% antiserum dilution; samples screened by AIR are equivalent to the samples studied for HAI during post-vaccination visit 2 (both results are bolded).

Although the preceding experiments were conducted using AIR as a label-free sensor platform, it should be appreciated by those of skill in the art that AIR is merely a preferred sensing platform because of its simplicity, sensitivity, and adaptability to large arrays of probe molecules (in this example, hemagglutinin isoforms). Indeed, use of an arrays sensor suitable for use in surface plasmon resonance ("SPR") detection systems, Brewster Angle Straddle Interferometry ("BASI"), ellipsometry, and any other label-free or fluorescence labeled array techniques is contemplated.

The rapid differentiation between clinically relevant naïve and generated immune states is a significant capability for any diagnostic assay, and more so if the platform is highly parallelized and quantitative. Towards this end, the utility of antigenic arrays for the determination of vaccine efficacy and viral surveillance of high-risk populations has been demonstrated by AIR. Like most biomolecular detection techniques (ELISA and SPR included), this simple direct assay lacks the ability to differentiate between inhibitory and broad, yet specific, antibody-ligand interactions; however, the tremendous sensitivity and selectivity of AIR can be exploited to probe the immunological contents of complex, subject-derived samples and augment the data acquired from traditional immune assays.

The incorporation of a robotic microarray instrument allowed arrays to be printed reproducibly, and in a high density, to allow more for more complex and informative assays to be performed. Moreover, the development of the G4 reflectometer permitted the microarrays to be clearly resolved and imaged. This proved to be a major technological advancement over the G3 reflectometer and a significant improvement toward optimization of these antigenic arrays.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. An arrayed imaging reflectometry (AIR) sensor chip suitable for the detection of influenza immune responses comprising:

a multilayer substrate comprising a surface and hemagglutinin polypeptides from different influenza strains or isolates, wherein said hemagglutinin polypeptides from each individual influenza strain or isolate comprise a hemagglutinin epitope and are covalently attached to the chip surface at different locations;

wherein said hemagglutinin polypeptides retain conformational epitopes that are capable of binding to anti-influenza antibodies;

wherein said surface with hemagglutinin polypeptides covalently attached at the different locations forms a coating on the chip surface that results in destructive interference of polarized light illuminating said surface at an appropriate incident angle and wavelength in the absence of antibody binding; and wherein exposure of the surface to a sample comprising anti-influenza antibodies produces a detectable change in reflectance at a location upon antigen-antibody binding.

2. The sensor chip according to claim 1, wherein the hemagglutinin polypeptides are full length hemagglutinin proteins.

3. The sensor chip according to claim 1, wherein the hemagglutinin polypeptides are fragments of full length hemagglutinin proteins.

4. The sensor chip according to claim 3, wherein the hemagglutinin polypeptide fragments each comprise an immunodominant hemagglutinin epitope of their respective native influenza strain.

5. The sensor chip according to claim 1, wherein the hemagglutinin polypeptides are covalently attached to the substrate via a glutaraldehyde linker.

6. The sensor chip according to claim 1, wherein each of said locations comprises a concentration of hemagglutinin polypeptide of about 100 $fg/mm^2$ to about 100 $ng/mm^2$.

7. The sensor chip according to claim 1 further comprising:

neuraminidase polypeptides from different influenza strains or isolates, wherein said neuraminidase polypeptides from each individual strain or isolate comprise a neuraminidase epitope and are covalently attached to the chip surface at different locations;

wherein said neuraminidase polypeptides retain conformational epitopes that are capable of binding to anti-influenza antibodies; and wherein said surface with neuraminidase polypeptides covalently attached at the different locations forms a coating on the chip surface that results in destructive interference of polarized light illuminating said surface at an appropriate incident angle and wavelength in the absence of antibody binding.

8. The sensor chip according to claim 7, wherein the neuraminidase polypeptides are full length neuraminidase proteins.

9. The sensor chip according to claim 7, wherein the neuraminidase polypeptides are fragments of full length neuraminidase proteins.

10. The sensor chip according to claim 9, wherein the neuraminidase polypeptide fragments each comprise an immunodominant neuraminidase epitope of their respective native influenza strain.

11. A method for detecting anti-influenza antibodies using arrayed imaging reflectometry (AIR), said method comprising:

providing a sensor chip according to claim 1;

contacting the sensor chip with a sample under conditions that permit specific anti-influenza antibody binding to the hemagglutinin polypeptides present on the chip surface;

rinsing the sensor chip to remove any unbound antibody; and detecting light reflected off the surface of the chip under conditions effective to identify anti-influenza antibody-antigen binding.

12. The method according to claim 11, wherein the sample is obtained from a human, a non-human primate, a domesticated animal, or a wild animal.

13. The method according to claim 11, wherein said detecting comprises:
 measuring light reflected from the chip and
 providing an output identifying the hemagglutinin polypeptides bound by an antibody of the sample based on the measured reflected light.

14. The method according to claim 13, wherein the measuring the reflected light further comprises capturing an image of at least a substantial portion of the surface of the chip.

* * * * *

SEQUENCE LISTING

```
<160> NUMBER OF SEQ ID NOS: 6

<210> SEQ ID NO 1
<211> LENGTH: 565
<212> TYPE: PRT
```

<213> ORGANISM: Influenza virus

<400> SEQUENCE: 1

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
```

-continued

```
                    405                 410                 415
Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 2
<211> LENGTH: 566
<212> TYPE: PRT
<213> ORGANISM: Influenza virus

<400> SEQUENCE: 2

Met Lys Thr Ile Ile Ala Leu Ser Tyr Ile Leu Cys Leu Val Phe Ser
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ala
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Ser Asp Gln Ile
        195                 200                 205

Ser Leu Tyr Ala Gln Ala Ser Gly Arg Ile Thr Val Ser Thr Lys Arg
```

```
            210                 215                 220
Ser Gln Gln Thr Val Ile Pro Asn Ile Gly Tyr Arg Pro Arg Val Arg
225                 230                 235                 240

Asp Ile Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Thr Gly Gln Ala Ala Asp Leu Lys
                370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
                530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 3
<211> LENGTH: 568
<212> TYPE: PRT
<213> ORGANISM: Influenza virus

<400> SEQUENCE: 3

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
```

```
                    20                  25                  30
Asp Thr Ile Met Glu Lys Asn Val Thr Val Thr His Ala Gln Asp Ile
                35                  40                  45

Leu Glu Lys Lys His Asn Gly Lys Leu Cys Asp Leu Asp Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Ser His Glu Ala Ser
        130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
        210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445
```

```
Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 4
<211> LENGTH: 566
<212> TYPE: PRT
<213> ORGANISM: Influenza virus

<400> SEQUENCE: 4

Met Ile Ala Ile Ile Val Ile Ala Ile Leu Ala Ala Ala Gly Lys Ser
1               5                   10                  15

Asp Lys Ile Cys Ile Gly Tyr His Ala Asn Asn Ser Thr Thr Gln Val
            20                  25                  30

Asp Thr Ile Leu Glu Lys Asn Val Thr Val Thr His Ser Ile Glu Leu
            35                  40                  45

Leu Glu Asn Gln Lys Glu Glu Arg Phe Cys Lys Ile Leu Asn Lys Ala
50                  55                  60

Pro Leu Asp Leu Arg Glu Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Thr Leu Asn
            100                 105                 110

Glu Val Glu Glu Leu Arg Ala Leu Ile Gly Ser Gly Glu Arg Val Glu
            115                 120                 125

Arg Phe Glu Met Phe Pro Gln Ser Thr Trp Gln Gly Val Asp Thr Asn
130                 135                 140

Ser Gly Thr Thr Arg Ser Cys Pro Tyr Ser Thr Gly Ala Ser Phe Tyr
145                 150                 155                 160

Arg Asn Leu Leu Trp Ile Ile Lys Thr Lys Thr Ala Glu Tyr Pro Val
                165                 170                 175

Ile Lys Gly Ile Tyr Asn Asn Thr Gly Thr Gln Pro Ile Leu Tyr Phe
            180                 185                 190

Trp Gly Val His His Pro Pro Asn Thr Asp Glu Gln Asp Thr Leu Tyr
            195                 200                 205

Gly Ser Gly Asp Arg Tyr Val Arg Met Gly Thr Glu Ser Met Asn Phe
210                 215                 220

Ala Lys Ser Pro Glu Ile Ala Ala Arg Pro Ala Val Asn Gly Gln Arg
225                 230                 235                 240

Gly Arg Ile Asp Tyr Tyr Trp Ser Val Leu Lys Pro Gly Glu Thr Leu
                245                 250                 255
```

Asn Val Glu Ser Asn Gly Asn Leu Ile Ala Pro Trp Tyr Ala Tyr Lys
260 265 270

Phe Val Asn Thr Asn Ser Lys Gly Ala Val Phe Arg Ser Asp Leu Pro
275 280 285

Ile Glu Asn Cys Asp Ala Thr Cys Gln Thr Ile Ala Gly Val Leu Arg
290 295 300

Thr Asn Lys Thr Phe Gln Asn Val Ser Pro Leu Trp Ile Gly Glu Cys
305 310 315 320

Pro Lys Tyr Val Lys Ser Glu Ser Leu Arg Leu Ala Thr Gly Leu Arg
325 330 335

Asn Val Pro Gln Ile Glu Thr Arg Gly Leu Phe Gly Ala Ile Ala Gly
340 345 350

Phe Ile Glu Gly Gly Trp Thr Gly Met Ile Asp Gly Trp Tyr Gly Tyr
355 360 365

His His Glu Asn Ser Gln Gly Ser Gly Tyr Ala Ala Asp Arg Glu Ser
370 375 380

Thr Gln Lys Ala Val Asn Arg Ile Thr Asn Lys Val Asn Ser Ile Ile
385 390 395 400

Asn Lys Met Asn Thr Gln Phe Glu Ala Val Asp His Glu Phe Ser Asn
405 410 415

Leu Glu Arg Arg Ile Asp Asn Leu Asn Lys Arg Met Gln Asp Gly Phe
420 425 430

Leu Asp Val Trp Thr Tyr Asn Ala Glu Leu Leu Val Leu Leu Glu Asn
435 440 445

Glu Arg Thr Leu Asp Met His Asp Ala Asn Val Lys Asn Leu His Glu
450 455 460

Lys Val Lys Ser Gln Leu Arg Asp Asn Ala Thr Ile Leu Gly Asn Gly
465 470 475 480

Cys Phe Glu Phe Trp His Lys Cys Asp Asn Glu Cys Ile Glu Ser Val
485 490 495

Lys Asn Gly Thr Tyr Asp Tyr Pro Lys Tyr Gln Thr Glu Ser Lys Leu
500 505 510

Asn Arg Leu Lys Ile Glu Ser Val Lys Leu Glu Asn Leu Gly Val Tyr
515 520 525

Gln Ile Leu Ala Ile Tyr Ser Thr Val Ser Ser Ser Leu Val Leu Val
530 535 540

Gly Leu Ile Met Ala Met Gly Leu Trp Met Cys Ser Asn Gly Ser Met
545 550 555 560

Gln Cys Arg Ile Cys Ile
565

<210> SEQ ID NO 5
<211> LENGTH: 560
<212> TYPE: PRT
<213> ORGANISM: Influenza virus

<400> SEQUENCE: 5

Met Glu Thr Ile Ser Leu Ile Thr Ile Leu Leu Val Val Thr Ala Ser
1 5 10 15

Asn Ala Asp Lys Ile Cys Ile Gly His Gln Ser Thr Asn Ser Thr Glu
20 25 30

Thr Val Asp Thr Leu Thr Glu Thr Asn Val Pro Val Thr His Ala Lys
35 40 45

Glu Leu Leu His Thr Glu His Asn Gly Met Leu Cys Ala Thr Ser Leu
50 55 60

```
Gly His Pro Leu Ile Leu Asp Thr Cys Thr Ile Glu Gly Leu Val Tyr
 65                  70                  75                  80

Gly Asn Pro Ser Cys Asp Leu Leu Leu Gly Arg Glu Trp Ser Tyr
                 85                  90                  95

Ile Val Glu Arg Ser Ser Ala Val Asn Gly Thr Cys Tyr Pro Gly Asn
                100                 105                 110

Val Glu Asn Leu Glu Glu Leu Arg Thr Leu Phe Ser Ser Ala Ser Ser
            115                 120                 125

Tyr Gln Arg Ile Gln Ile Phe Pro Asp Thr Thr Trp Asn Val Thr Tyr
        130                 135                 140

Thr Gly Thr Ser Arg Ala Cys Ser Gly Ser Phe Tyr Arg Ser Met Arg
145                 150                 155                 160

Trp Leu Thr Gln Lys Ser Gly Phe Tyr Pro Val Gln Asp Ala Gln Tyr
                165                 170                 175

Thr Asn Asn Arg Gly Lys Ser Ile Leu Phe Val Trp Gly Ile His His
                180                 185                 190

Pro Pro Thr Tyr Thr Glu Gln Thr Asn Leu Tyr Ile Arg Asn Asp Thr
            195                 200                 205

Thr Thr Ser Val Thr Thr Glu Asp Leu Asn Arg Thr Phe Lys Pro Val
210                 215                 220

Ile Gly Pro Arg Pro Leu Val Asn Gly Leu Gln Gly Arg Ile Asp Tyr
225                 230                 235                 240

Tyr Trp Ser Val Leu Lys Pro Gly Gln Thr Leu Arg Val Arg Ser Asn
                245                 250                 255

Gly Asn Leu Ile Ala Pro Trp Tyr Gly His Val Leu Ser Gly Gly Ser
                260                 265                 270

His Gly Arg Ile Leu Lys Thr Asp Leu Lys Gly Gly Asn Cys Val Val
                275                 280                 285

Gln Cys Gln Thr Glu Lys Gly Gly Leu Asn Ser Thr Leu Pro Phe His
290                 295                 300

Asn Ile Ser Lys Tyr Ala Phe Gly Thr Cys Pro Lys Tyr Val Arg Val
305                 310                 315                 320

Asn Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
                340                 345                 350

Pro Gly Leu Val Ala Gly Trp Tyr Gly Phe Gln His Ser Asn Asp Gln
                355                 360                 365

Gly Val Gly Met Ala Ala Asp Arg Asp Ser Thr Gln Lys Ala Ile Asp
            370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Thr Arg Leu Asn
                405                 410                 415

Met Ile Asn Asn Lys Ile Asp Asp Gln Ile Gln Asp Val Trp Ala Tyr
                420                 425                 430

Asn Ala Glu Leu Leu Val Leu Leu Glu Asn Gln Lys Thr Leu Asp Glu
            435                 440                 445

His Asp Ala Asn Val Asn Asn Leu Tyr Asn Lys Val Lys Arg Ala Leu
450                 455                 460

Gly Ser Asn Ala Met Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495
```

```
Arg Arg Lys Tyr Arg Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Leu Ala Met Gly Phe Ala Ala Phe
    530                 535                 540

Leu Phe Trp Ala Met Ser Asn Gly Ser Cys Arg Cys Asn Ile Cys Ile
545                 550                 555                 560

<210> SEQ ID NO 6
<211> LENGTH: 576
<212> TYPE: PRT
<213> ORGANISM: Artificial
<220> FEATURE:
<223> OTHER INFORMATION: Multalin Consensus of SEQ ID NOS: 1-5
<220> FEATURE:
<221> NAME/KEY: MISC_FEATURE
<222> LOCATION: (1)..(18)
<223> OTHER INFORMATION: X at positions 1-18 are optional and can be any
      amino acid
<220> FEATURE:
<221> NAME/KEY: MISC_FEATURE
<222> LOCATION: (20)..(22)
<223> OTHER INFORMATION: X at positions 20-22 can be any amino acid
<220> FEATURE:
<221> NAME/KEY: MISC_FEATURE
<222> LOCATION: (24)..(26)
<223> OTHER INFORMATION: X at positions 24-26 can be any amino acid
<220> FEATURE:
<221> NAME/KEY: MISC_FEATURE
<222> LOCATION: (28)..(28)
<223> OTHER INFORMATION: X at position 28 can be any amino acid
<220> FEATURE:
<221> NAME/KEY: MISC_FEATURE
<222> LOCATION: (36)..(36)
<223> OTHER INFORMATION: X at position 36 can be any amino acid
<220> FEATURE:
<221> NAME/KEY: MISC_FEATURE
<222> LOCATION: (41)..(41)
<223> OTHER INFORMATION: X at position 41 can be any amino acid
<220> FEATURE:
<221> NAME/KEY: MISC_FEATURE
<222> LOCATION: (47)..(47)
<223> OTHER INFORMATION: X at position 47 can be Asn, Asp, Glu, Gln,
      Asx, or Glx
<220> FEATURE:
<221> NAME/KEY: MISC_FEATURE
<222> LOCATION: (48)..(48)
<223> OTHER INFORMATION: X at position 48 can be any amino acid
<220> FEATURE:
<221> NAME/KEY: MISC_FEATURE
<222> LOCATION: (49)..(49)
<223> OTHER INFORMATION: X at position 49 can be Asn, Asp, Glu, Gln,
      Asx, or Glx
<220> FEATURE:
<221> NAME/KEY: MISC_FEATURE
<222> LOCATION: (50)..(50)
<223> OTHER INFORMATION: X at position 50 can be Ile or Val
<220> FEATURE:
<221> NAME/KEY: MISC_FEATURE
<222> LOCATION: (51)..(51)
<223> OTHER INFORMATION: X at position 51 can be any amino acid
<220> FEATURE:
<221> NAME/KEY: MISC_FEATURE
<222> LOCATION: (56)..(56)
<223> OTHER INFORMATION: X at position 56 can be any amino acid
<220> FEATURE:
<221> NAME/KEY: MISC_FEATURE
<222> LOCATION: (57)..(57)
<223> OTHER INFORMATION: X at position 57 can be Asn, Asp, Glu, Gln,
      Asx, or Glx
<220> FEATURE:
<221> NAME/KEY: MISC_FEATURE
<222> LOCATION: (60)..(64)
<223> OTHER INFORMATION: X at positions 60-64 can be any amino acid
```

-continued

```
<220> FEATURE:
<221> NAME/KEY: MISC_FEATURE
<222> LOCATION: (66)..(67)
<223> OTHER INFORMATION: X at positions 66-67 can be any amino acid
<220> FEATURE:
<221> NAME/KEY: MISC_FEATURE
<222> LOCATION: (69)..(70)
<223> OTHER INFORMATION: X at positions 69-70 can be any amino acid
<220> FEATURE:
<221> NAME/KEY: MISC_FEATURE
<222> LOCATION: (72)..(74)
<223> OTHER INFORMATION: X at positions 72-74 can be any amino acid
<220> FEATURE:
<221> NAME/KEY: MISC_FEATURE
<222> LOCATION: (79)..(80)
<223> OTHER INFORMATION: X at positions 79-80 can be any amino acid
<220> FEATURE:
<221> NAME/KEY: MISC_FEATURE
<222> LOCATION: (83)..(84)
<223> OTHER INFORMATION: X at positions 83-84 can be any amino acid
<220> FEATURE:
<221> NAME/KEY: MISC_FEATURE
<222> LOCATION: (86)..(87)
<223> OTHER INFORMATION: X at positions 86-87 can be any amino acid
<220> FEATURE:
<221> NAME/KEY: MISC_FEATURE
<222> LOCATION: (90)..(90)
<223> OTHER INFORMATION: X at position 90 can be Asn, Asp, Glu, Gln,
      Asx, or Glx
<220> FEATURE:
<221> NAME/KEY: MISC_FEATURE
<222> LOCATION: (97)..(101)
<223> OTHER INFORMATION: X at positions 97-101 can be any amino acid
<220> FEATURE:
<221> NAME/KEY: MISC_FEATURE
<222> LOCATION: (110)..(110)
<223> OTHER INFORMATION: X at position 110 can be any amino acid
<220> FEATURE:
<221> NAME/KEY: MISC_FEATURE
<222> LOCATION: (112)..(112)
<223> OTHER INFORMATION: X at position 112 can be any amino acid
<220> FEATURE:
<221> NAME/KEY: MISC_FEATURE
<222> LOCATION: (115)..(115)
<223> OTHER INFORMATION: X at position 115 can be any amino acid
<220> FEATURE:
<221> NAME/KEY: MISC_FEATURE
<222> LOCATION: (120)..(120)
<223> OTHER INFORMATION: X at position 120 can be any amino acid
<220> FEATURE:
<221> NAME/KEY: MISC_FEATURE
<222> LOCATION: (122)..(122)
<223> OTHER INFORMATION: X at position 122 can be any amino acid
<220> FEATURE:
<221> NAME/KEY: MISC_FEATURE
<222> LOCATION: (123)..(123)
<223> OTHER INFORMATION: X at position 123 can be Asn, Asp, Glu, Gln,
      Asx, or Glx
<220> FEATURE:
<221> NAME/KEY: MISC_FEATURE
<222> LOCATION: (129)..(129)
<223> OTHER INFORMATION: X at position 129 can be any amino acid
<220> FEATURE:
<221> NAME/KEY: MISC_FEATURE
<222> LOCATION: (131)..(132)
<223> OTHER INFORMATION: X at positions 131-132 can be any amino acid
<220> FEATURE:
<221> NAME/KEY: MISC_FEATURE
<222> LOCATION: (134)..(138)
<223> OTHER INFORMATION: X at positions 134-138 can be any amino acid
<220> FEATURE:
<221> NAME/KEY: MISC_FEATURE
<222> LOCATION: (140)..(140)
<223> OTHER INFORMATION: X at position 140 can be any amino acid
<220> FEATURE:
<221> NAME/KEY: MISC_FEATURE
<222> LOCATION: (141)..(141)
<223> OTHER INFORMATION: X at position 141 can be Asn, Asp, Glu, Gln,
      Asx, or Glx
<220> FEATURE:
```

```
<221> NAME/KEY: MISC_FEATURE
<222> LOCATION: (142)..(142)
<223> OTHER INFORMATION: X at position 142 can be any amino acid
<220> FEATURE:
<221> NAME/KEY: MISC_FEATURE
<222> LOCATION: (145)..(145)
<223> OTHER INFORMATION: X at position 145 can be any amino acid
<220> FEATURE:
<221> NAME/KEY: MISC_FEATURE
<222> LOCATION: (147)..(147)
<223> OTHER INFORMATION: X at position 147 can be any amino acid
<220> FEATURE:
<221> NAME/KEY: MISC_FEATURE
<222> LOCATION: (149)..(151)
<223> OTHER INFORMATION: X at positions 149-151 can be any amino acid
<220> FEATURE:
<221> NAME/KEY: MISC_FEATURE
<222> LOCATION: (154)..(155)
<223> OTHER INFORMATION: X at positions 154-155 can be any amino acid
<220> FEATURE:
<221> NAME/KEY: MISC_FEATURE
<222> LOCATION: (159)..(159)
<223> OTHER INFORMATION: X at position 159 can be any amino acid
<220> FEATURE:
<221> NAME/KEY: MISC_FEATURE
<222> LOCATION: (162)..(167)
<223> OTHER INFORMATION: X at positions 162-167 can be any amino acid
<220> FEATURE:
<221> NAME/KEY: MISC_FEATURE
<222> LOCATION: (170)..(170)
<223> OTHER INFORMATION: X at position 170 can be Phe or Tyr
<220> FEATURE:
<221> NAME/KEY: MISC_FEATURE
<222> LOCATION: (172)..(172)
<223> OTHER INFORMATION: X at position 172 can be any amino acid
<220> FEATURE:
<221> NAME/KEY: MISC_FEATURE
<222> LOCATION: (173)..(173)
<223> OTHER INFORMATION: X at position 173 can be Leu or Met
<220> FEATURE:
<221> NAME/KEY: MISC_FEATURE
<222> LOCATION: (174)..(174)
<223> OTHER INFORMATION: X at position 174 can be any amino acid
<220> FEATURE:
<221> NAME/KEY: MISC_FEATURE
<222> LOCATION: (178)..(179)
<223> OTHER INFORMATION: X at positions 178-179 can be any amino acid
<220> FEATURE:
<221> NAME/KEY: MISC_FEATURE
<222> LOCATION: (181)..(183)
<223> OTHER INFORMATION: X at positions 181-183 can be any amino acid
<220> FEATURE:
<221> NAME/KEY: MISC_FEATURE
<222> LOCATION: (186)..(190)
<223> OTHER INFORMATION: X at positions 186-190 can be any amino acid
<220> FEATURE:
<221> NAME/KEY: MISC_FEATURE
<222> LOCATION: (192)..(192)
<223> OTHER INFORMATION: X at position 192 can be any amino acid
<220> FEATURE:
<221> NAME/KEY: MISC_FEATURE
<222> LOCATION: (195)..(199)
<223> OTHER INFORMATION: X at positions 195-199 can be any amino acid
<220> FEATURE:
<221> NAME/KEY: MISC_FEATURE
<222> LOCATION: (202)..(202)
<223> OTHER INFORMATION: X at position 202 can be any amino acid
<220> FEATURE:
<221> NAME/KEY: MISC_FEATURE
<222> LOCATION: (205)..(205)
<223> OTHER INFORMATION: X at position 205 can be Ile or Val
<220> FEATURE:
<221> NAME/KEY: MISC_FEATURE
<222> LOCATION: (211)..(212)
<223> OTHER INFORMATION: X at positions 211-212 can be any amino acid
<220> FEATURE:
<221> NAME/KEY: MISC_FEATURE
<222> LOCATION: (213)..(213)
<223> OTHER INFORMATION: X at position 213 can be Asn, Asp, Glu, Gln,
      Asx, or Glx
```

-continued

```
<220> FEATURE:
<221> NAME/KEY: MISC_FEATURE
<222> LOCATION: (215)..(216)
<223> OTHER INFORMATION: X at positions 215-216 can be any amino acid
<220> FEATURE:
<221> NAME/KEY: MISC_FEATURE
<222> LOCATION: (219)..(226)
<223> OTHER INFORMATION: X at positions 219-226 can be any amino acid
<220> FEATURE:
<221> NAME/KEY: MISC_FEATURE
<222> LOCATION: (228)..(228)
<223> OTHER INFORMATION: X at position 228 can be any amino acid
<220> FEATURE:
<221> NAME/KEY: MISC_FEATURE
<222> LOCATION: (230)..(232)
<223> OTHER INFORMATION: X at positions 230-232 can be any amino acid
<220> FEATURE:
<221> NAME/KEY: MISC_FEATURE
<222> LOCATION: (233)..(233)
<223> OTHER INFORMATION: X at position 233 can be Asn, Asp, Glu, Gln,
      Asx, or Glx
<220> FEATURE:
<221> NAME/KEY: MISC_FEATURE
<222> LOCATION: (234)..(234)
<223> OTHER INFORMATION: X at position 234 can be any amino acid
<220> FEATURE:
<221> NAME/KEY: MISC_FEATURE
<222> LOCATION: (236)..(237)
<223> OTHER INFORMATION: X at positions 236-237 can be any amino acid
<220> FEATURE:
<221> NAME/KEY: MISC_FEATURE
<222> LOCATION: (239)..(239)
<223> OTHER INFORMATION: X at position 239 can be any amino acid
<220> FEATURE:
<221> NAME/KEY: MISC_FEATURE
<222> LOCATION: (242)..(242)
<223> OTHER INFORMATION: X at position 242 can be any amino acid
<220> FEATURE:
<221> NAME/KEY: MISC_FEATURE
<222> LOCATION: (245)..(245)
<223> OTHER INFORMATION: X at position 245 can be any amino acid
<220> FEATURE:
<221> NAME/KEY: MISC_FEATURE
<222> LOCATION: (249)..(250)
<223> OTHER INFORMATION: X at positions 249-250 can be any amino acid
<220> FEATURE:
<221> NAME/KEY: MISC_FEATURE
<222> LOCATION: (254)..(254)
<223> OTHER INFORMATION: X at position 254 can be any amino acid
<220> FEATURE:
<221> NAME/KEY: MISC_FEATURE
<222> LOCATION: (259)..(259)
<223> OTHER INFORMATION: X at position 259 can be Ile or Val
<220> FEATURE:
<221> NAME/KEY: MISC_FEATURE
<222> LOCATION: (264)..(264)
<223> OTHER INFORMATION: X at position 264 can be Asn, Asp, Glu, Gln,
      Asx, or Glx
<220> FEATURE:
<221> NAME/KEY: MISC_FEATURE
<222> LOCATION: (267)..(269)
<223> OTHER INFORMATION: X at positions 267-269 can be any amino acid
<220> FEATURE:
<221> NAME/KEY: MISC_FEATURE
<222> LOCATION: (280)..(281)
<223> OTHER INFORMATION: X at positions 280-281 can be any amino acid
<220> FEATURE:
<221> NAME/KEY: MISC_FEATURE
<222> LOCATION: (283)..(284)
<223> OTHER INFORMATION: X at positions 283-284 can be any amino acid
<220> FEATURE:
<221> NAME/KEY: MISC_FEATURE
<222> LOCATION: (287)..(287)
<223> OTHER INFORMATION: X at position 287 can be any amino acid
<220> FEATURE:
<221> NAME/KEY: MISC_FEATURE
<222> LOCATION: (291)..(291)
<223> OTHER INFORMATION: X at position 291 can be any amino acid
<220> FEATURE:
<221> NAME/KEY: MISC_FEATURE
```

```
<222> LOCATION: (292)..(292)
<223> OTHER INFORMATION: X at position 292 can be Ile or Val
<220> FEATURE:
<221> NAME/KEY: MISC_FEATURE
<222> LOCATION: (293)..(293)
<223> OTHER INFORMATION: X at position 293 can be any amino acid
<220> FEATURE:
<221> NAME/KEY: MISC_FEATURE
<222> LOCATION: (296)..(296)
<223> OTHER INFORMATION: X at position 296 can be Asn, Asp, Glu, Gln,
      Asx, or Glx
<220> FEATURE:
<221> NAME/KEY: MISC_FEATURE
<222> LOCATION: (303)..(305)
<223> OTHER INFORMATION: X at positions 303-305 can be any amino acid
<220> FEATURE:
<221> NAME/KEY: MISC_FEATURE
<222> LOCATION: (310)..(310)
<223> OTHER INFORMATION: X at position 310 can be any amino acid
<220> FEATURE:
<221> NAME/KEY: MISC_FEATURE
<222> LOCATION: (312)..(312)
<223> OTHER INFORMATION: X at position 312 can be any amino acid
<220> FEATURE:
<221> NAME/KEY: MISC_FEATURE
<222> LOCATION: (314)..(316)
<223> OTHER INFORMATION: X at positions 314-316 can be any amino acid
<220> FEATURE:
<221> NAME/KEY: MISC_FEATURE
<222> LOCATION: (322)..(322)
<223> OTHER INFORMATION: X at position 322 can be Ile or Val
<220> FEATURE:
<221> NAME/KEY: MISC_FEATURE
<222> LOCATION: (323)..(325)
<223> OTHER INFORMATION: X at positions 323-325 can be any amino acid
<220> FEATURE:
<221> NAME/KEY: MISC_FEATURE
<222> LOCATION: (327)..(327)
<223> OTHER INFORMATION: X at position 327 can be any amino acid
<220> FEATURE:
<221> NAME/KEY: MISC_FEATURE
<222> LOCATION: (329)..(329)
<223> OTHER INFORMATION: X at position 329 can be any amino acid
<220> FEATURE:
<221> NAME/KEY: MISC_FEATURE
<222> LOCATION: (336)..(336)
<223> OTHER INFORMATION: X at position 336 can be any amino acid
<220> FEATURE:
<221> NAME/KEY: MISC_FEATURE
<222> LOCATION: (337)..(337)
<223> OTHER INFORMATION: X at position 337 can be Asn, Asp, Glu, Gln,
      Asx, or Glx
<220> FEATURE:
<221> NAME/KEY: MISC_FEATURE
<222> LOCATION: (338)..(338)
<223> OTHER INFORMATION: X at position 338 can be any amino acid
<220> FEATURE:
<221> NAME/KEY: MISC_FEATURE
<222> LOCATION: (345)..(345)
<223> OTHER INFORMATION: X at position 345 can be Leu or Met
<220> FEATURE:
<221> NAME/KEY: MISC_FEATURE
<222> LOCATION: (348)..(348)
<223> OTHER INFORMATION: X at position 348 can be Ile or Val
<220> FEATURE:
<221> NAME/KEY: MISC_FEATURE
<222> LOCATION: (350)..(352)
<223> OTHER INFORMATION: X at positions 350-352 can be any amino acid
<220> FEATURE:
<221> NAME/KEY: MISC_FEATURE
<222> LOCATION: (369)..(369)
<223> OTHER INFORMATION: X at position 369 can be any amino acid
<220> FEATURE:
<221> NAME/KEY: MISC_FEATURE
<222> LOCATION: (371)..(371)
<223> OTHER INFORMATION: X at position 371 can be Leu or Met
<220> FEATURE:
<221> NAME/KEY: MISC_FEATURE
<222> LOCATION: (372)..(372)
<223> OTHER INFORMATION: X can be Ile or Val
```

```
<220> FEATURE:
<221> NAME/KEY: MISC_FEATURE
<222> LOCATION: (378)..(378)
<223> OTHER INFORMATION: X at position 378 can be Phe or Tyr
<220> FEATURE:
<221> NAME/KEY: MISC_FEATURE
<222> LOCATION: (379)..(379)
<223> OTHER INFORMATION: X at position 379 can be any amino acid
<220> FEATURE:
<221> NAME/KEY: MISC_FEATURE
<222> LOCATION: (381)..(381)
<223> OTHER INFORMATION: X at position 381 can be any amino acid
<220> FEATURE:
<221> NAME/KEY: MISC_FEATURE
<222> LOCATION: (384)..(384)
<223> OTHER INFORMATION: X at position 384 can be Asn, Asp, Glu, Gln,
      Asx, or Glx
<220> FEATURE:
<221> NAME/KEY: MISC_FEATURE
<222> LOCATION: (386)..(386)
<223> OTHER INFORMATION: X at position 386 can be any amino acid
<220> FEATURE:
<221> NAME/KEY: MISC_FEATURE
<222> LOCATION: (388)..(388)
<223> OTHER INFORMATION: X at position 388 can be any amino acid
<220> FEATURE:
<221> NAME/KEY: MISC_FEATURE
<222> LOCATION: (392)..(393)
<223> OTHER INFORMATION: X at positions 392-393 can be any amino acid
<220> FEATURE:
<221> NAME/KEY: MISC_FEATURE
<222> LOCATION: (399)..(399)
<223> OTHER INFORMATION: X at position 399 can be Ile or Val
<220> FEATURE:
<221> NAME/KEY: MISC_FEATURE
<222> LOCATION: (400)..(400)
<223> OTHER INFORMATION: X at position 400 can be Asn, Asp, Glu, Gln,
      Asx, or Glx
<220> FEATURE:
<221> NAME/KEY: MISC_FEATURE
<222> LOCATION: (401)..(401)
<223> OTHER INFORMATION: X at position 401 can be any amino acid
<220> FEATURE:
<221> NAME/KEY: MISC_FEATURE
<222> LOCATION: (404)..(404)
<223> OTHER INFORMATION: X at position 404 can be any amino acid
<220> FEATURE:
<221> NAME/KEY: MISC_FEATURE
<222> LOCATION: (408)..(408)
<223> OTHER INFORMATION: X at position 408 can be any amino acid
<220> FEATURE:
<221> NAME/KEY: MISC_FEATURE
<222> LOCATION: (410)..(410)
<223> OTHER INFORMATION: X at position 410 can be Ile or Val
<220> FEATURE:
<221> NAME/KEY: MISC_FEATURE
<222> LOCATION: (411)..(411)
<223> OTHER INFORMATION: X at position 411 can be any amino acid
<220> FEATURE:
<221> NAME/KEY: MISC_FEATURE
<222> LOCATION: (415)..(415)
<223> OTHER INFORMATION: X at position 415 can be any amino acid
<220> FEATURE:
<221> NAME/KEY: MISC_FEATURE
<222> LOCATION: (417)..(417)
<223> OTHER INFORMATION: X at position 417 can be Phe or Tyr
<220> FEATURE:
<221> NAME/KEY: MISC_FEATURE
<222> LOCATION: (419)..(419)
<223> OTHER INFORMATION: X at position 419 can be any amino acid
<220> FEATURE:
<221> NAME/KEY: MISC_FEATURE
<222> LOCATION: (420)..(420)
<223> OTHER INFORMATION: X at position 420 can be Ile or Val
<220> FEATURE:
<221> NAME/KEY: MISC_FEATURE
<222> LOCATION: (421)..(422)
<223> OTHER INFORMATION: X at positions 421-422 can be any amino acid
<220> FEATURE:
<221> NAME/KEY: MISC_FEATURE
```

```
<222> LOCATION: (426)..(426)
<223> OTHER INFORMATION: X at position 426 can be Asn, Asp, Glu, Gln,
      Asx, or Glx
<220> FEATURE:
<221> NAME/KEY: MISC_FEATURE
<222> LOCATION: (429)..(429)
<223> OTHER INFORMATION: X at position 429 can be any amino acid
<220> FEATURE:
<221> NAME/KEY: MISC_FEATURE
<222> LOCATION: (432)..(432)
<223> OTHER INFORMATION: X at position 432 can be Asn, Asp, Glu, Gln,
      Asx, or Glx
<220> FEATURE:
<221> NAME/KEY: MISC_FEATURE
<222> LOCATION: (433)..(433)
<223> OTHER INFORMATION: X at position 433 can be any amino acid
<220> FEATURE:
<221> NAME/KEY: MISC_FEATURE
<222> LOCATION: (435)..(435)
<223> OTHER INFORMATION: X at position 435 can be Asn, Asp, Glu, Gln,
      Asx, or Glx
<220> FEATURE:
<221> NAME/KEY: MISC_FEATURE
<222> LOCATION: (437)..(438)
<223> OTHER INFORMATION: X at positions 437-438 can be any amino acid
<220> FEATURE:
<221> NAME/KEY: MISC_FEATURE
<222> LOCATION: (439)..(439)
<223> OTHER INFORMATION: X at position 439 can be Asn, Asp, Glu, Gln,
      Asx, or Glx
<220> FEATURE:
<221> NAME/KEY: MISC_FEATURE
<222> LOCATION: (441)..(443)
<223> OTHER INFORMATION: X at positions 441-443 can be any amino acid
<220> FEATURE:
<221> NAME/KEY: MISC_FEATURE
<222> LOCATION: (447)..(447)
<223> OTHER INFORMATION: X at position 447 can be any amino acid
<220> FEATURE:
<221> NAME/KEY: MISC_FEATURE
<222> LOCATION: (459)..(459)
<223> OTHER INFORMATION: X at position 459 can be Asn, Asp, Glu, Gln,
      Asx, or Glx
<220> FEATURE:
<221> NAME/KEY: MISC_FEATURE
<222> LOCATION: (460)..(460)
<223> OTHER INFORMATION: X at position 460 can be any amino acid
<220> FEATURE:
<221> NAME/KEY: MISC_FEATURE
<222> LOCATION: (464)..(464)
<223> OTHER INFORMATION: X at position 464 can be any amino acid
<220> FEATURE:
<221> NAME/KEY: MISC_FEATURE
<222> LOCATION: (468)..(468)
<223> OTHER INFORMATION: X at position 468 can be Asn, Asp, Glu, Gln,
      Asx, or Glx
<220> FEATURE:
<221> NAME/KEY: MISC_FEATURE
<222> LOCATION: (473)..(473)
<223> OTHER INFORMATION: X at position 473 can be any amino acid
<220> FEATURE:
<221> NAME/KEY: MISC_FEATURE
<222> LOCATION: (474)..(474)
<223> OTHER INFORMATION: X at position 474 can be Asn, Asp, Glu, Gln,
      Asx, or Glx
<220> FEATURE:
<221> NAME/KEY: MISC_FEATURE
<222> LOCATION: (478)..(478)
<223> OTHER INFORMATION: X at position 478 can be any amino acid
<220> FEATURE:
<221> NAME/KEY: MISC_FEATURE
<222> LOCATION: (482)..(482)
<223> OTHER INFORMATION: X at position 482 can be any amino acid
<220> FEATURE:
<221> NAME/KEY: MISC_FEATURE
<222> LOCATION: (485)..(487)
<223> OTHER INFORMATION: X at positions 485-487 can be any amino acid
<220> FEATURE:
<221> NAME/KEY: MISC_FEATURE
<222> LOCATION: (494)..(494)
```

-continued

```
<223> OTHER INFORMATION: X at position 494 can be any amino acid
<220> FEATURE:
<221> NAME/KEY: MISC_FEATURE
<222> LOCATION: (500)..(500)
<223> OTHER INFORMATION: X at position 500 can be Asn, Asp, Glu, Gln,
      Asx, or Glx
<220> FEATURE:
<221> NAME/KEY: MISC_FEATURE
<222> LOCATION: (501)..(501)
<223> OTHER INFORMATION: X at position 501 can be any amino acid
<220> FEATURE:
<221> NAME/KEY: MISC_FEATURE
<222> LOCATION: (506)..(506)
<223> OTHER INFORMATION: X at position 506 can be Ile or Val
<220> FEATURE:
<221> NAME/KEY: MISC_FEATURE
<222> LOCATION: (512)..(512)
<223> OTHER INFORMATION: X at position 512 can be Asn, Asp, Glu, Gln,
      Asx, or Glx
<220> FEATURE:
<221> NAME/KEY: MISC_FEATURE
<222> LOCATION: (513)..(514)
<223> OTHER INFORMATION: X at positions 513-514 can be any amino acid
<220> FEATURE:
<221> NAME/KEY: MISC_FEATURE
<222> LOCATION: (518)..(518)
<223> OTHER INFORMATION: X at position 518 can be any amino acid
<220> FEATURE:
<221> NAME/KEY: MISC_FEATURE
<222> LOCATION: (521)..(521)
<223> OTHER INFORMATION: X at position 521 can be any amino acid
<220> FEATURE:
<221> NAME/KEY: MISC_FEATURE
<222> LOCATION: (523)..(523)
<223> OTHER INFORMATION: X at position 523 can be Asn, Asp, Glu, Gln,
      Asx, or Glx
<220> FEATURE:
<221> NAME/KEY: MISC_FEATURE
<222> LOCATION: (525)..(525)
<223> OTHER INFORMATION: X at position 525 can be any amino acid
<220> FEATURE:
<221> NAME/KEY: MISC_FEATURE
<222> LOCATION: (528)..(528)
<223> OTHER INFORMATION: X at position 528 can be any amino acid
<220> FEATURE:
<221> NAME/KEY: MISC_FEATURE
<222> LOCATION: (535)..(535)
<223> OTHER INFORMATION: X at position 535 can be any amino acid
<220> FEATURE:
<221> NAME/KEY: MISC_FEATURE
<222> LOCATION: (537)..(537)
<223> OTHER INFORMATION: X at position 537 can be any amino acid
<220> FEATURE:
<221> NAME/KEY: MISC_FEATURE
<222> LOCATION: (539)..(539)
<223> OTHER INFORMATION: X at position 539 can be any amino acid
<220> FEATURE:
<221> NAME/KEY: MISC_FEATURE
<222> LOCATION: (542)..(542)
<223> OTHER INFORMATION: X at position 542 can be any amino acid
<220> FEATURE:
<221> NAME/KEY: MISC_FEATURE
<222> LOCATION: (548)..(548)
<223> OTHER INFORMATION: X at position 548 can be any amino acid
<220> FEATURE:
<221> NAME/KEY: MISC_FEATURE
<222> LOCATION: (554)..(558)
<223> OTHER INFORMATION: X at positions 554-558 can be any amino acid
<220> FEATURE:
<221> NAME/KEY: MISC_FEATURE
<222> LOCATION: (561)..(562)
<223> OTHER INFORMATION: X at positions 561-562 can be any amino acid
<220> FEATURE:
<221> NAME/KEY: MISC_FEATURE
<222> LOCATION: (570)..(570)
<223> OTHER INFORMATION: X at position 570 can be any amino acid

<400> SEQUENCE: 6

Xaa Xaa Xaa Xaa Xaa Xaa Xaa Xaa Xaa Xaa Xaa Xaa Xaa Xaa Xaa Xaa
```

-continued

```
1               5                   10                  15
Xaa Xaa Leu Xaa Xaa Ala Xaa Xaa Xaa Asp Xaa Ile Cys Ile Gly
            20                  25                  30

His His Ala Xaa Asn Ser Thr Thr Xaa Val Asp Thr Ile Thr Xaa Xaa
            35                  40                  45

Xaa Xaa Xaa Val Thr His Ala Xaa Xaa Leu Leu Xaa Xaa Xaa Xaa
        50                  55                  60

Gly Xaa Xaa Cys Xaa Xaa Ser Xaa Xaa Xaa Pro Leu Asp Leu Xaa Xaa
65                  70                  75                  80

Cys Thr Xaa Xaa Gly Xaa Xaa Leu Gly Xaa Pro Gln Cys Asp Leu Leu
                85                  90                  95

Xaa Xaa Xaa Xaa Xaa Trp Ser Tyr Ile Val Glu Arg Ser Xaa Ala Xaa
            100                 105                 110

Asn Gly Xaa Cys Tyr Pro Gly Xaa Val Xaa Xaa Tyr Glu Glu Leu Arg
        115                 120                 125

Xaa Leu Xaa Xaa Ser Xaa Xaa Xaa Xaa Arg Xaa Xaa Xaa Phe Pro
        130                 135                 140

Xaa Ser Xaa Trp Xaa Xaa Xaa Val Thr Xaa Xaa Gly Thr Ser Xaa Ala
145                 150                 155                 160

Cys Xaa Xaa Xaa Xaa Xaa Xaa Ser Phe Xaa Arg Xaa Xaa Xaa Trp Leu
            165                 170                 175

Thr Xaa Xaa Lys Xaa Xaa Xaa Tyr Pro Xaa Xaa Xaa Xaa Tyr Xaa
        180                 185                 190

Asn Asn Xaa Xaa Xaa Xaa Xaa Leu Tyr Xaa Trp Gly Xaa His His Pro
        195                 200                 205

Pro Thr Xaa Xaa Xaa Gln Xaa Xaa Leu Tyr Xaa Xaa Xaa Xaa Xaa Xaa
        210                 215                 220

Xaa Xaa Val Xaa Thr Xaa Xaa Xaa Xaa Thr Xaa Xaa Pro Xaa Ile
225                 230                 235                 240

Gly Xaa Arg Pro Xaa Val Asn Gly Xaa Xaa Gly Arg Ile Xaa Tyr Tyr
            245                 250                 255

Trp Thr Xaa Leu Lys Pro Gly Xaa Thr Leu Xaa Xaa Xaa Ser Asn Gly
            260                 265                 270

Asn Leu Ile Ala Pro Trp Tyr Xaa Xaa Lys Xaa Xaa Ser Gly Xaa Ser
        275                 280                 285

Ser Gly Xaa Xaa Xaa Arg Ser Xaa Leu Pro Ile Gly Asn Cys Xaa Xaa
        290                 295                 300

Xaa Cys Gln Thr Pro Xaa Gly Xaa Ile Xaa Xaa Xaa Lys Pro Phe Gln
305                 310                 315                 320

Asn Xaa Xaa Xaa Xaa Thr Xaa Gly Xaa Cys Pro Lys Tyr Val Lys Xaa
            325                 330                 335

Xaa Xaa Leu Lys Leu Ala Thr Gly Xaa Arg Asn Xaa Pro Xaa Xaa Xaa
        340                 345                 350

Thr Arg Gly Leu Phe Gly Ala Ile Ala Gly Phe Ile Glu Gly Gly Trp
        355                 360                 365

Xaa Gly Xaa Xaa Asp Gly Trp Tyr Gly Xaa Xaa His Xaa Asn Ser Xaa
        370                 375                 380

Gly Xaa Gly Xaa Ala Ala Asp Xaa Xaa Ser Thr Gln Lys Ala Xaa Xaa
385                 390                 395                 400

Xaa Ile Thr Xaa Lys Val Asn Xaa Ile Xaa Xaa Lys Met Asn Xaa Gln
            405                 410                 415

Xaa Glu Xaa Xaa Xaa Xaa Glu Phe Ser Xaa Val Glu Xaa Arg Ile Xaa
            420                 425                 430
```

-continued

```
Xaa Leu Xaa Lys Xaa Xaa Xaa Asp Xaa Xaa Xaa Asp Val Trp Xaa Tyr
        435                 440                 445

Asn Ala Glu Leu Leu Val Leu Leu Glu Asn Xaa Xaa Thr Leu Asp Xaa
    450                 455                 460

His Asp Ser Xaa Val Asn Asn Leu Xaa Xaa Lys Val Lys Xaa Gln Leu
465                 470                 475                 480

Arg Xaa Asn Ala Xaa Xaa Xaa Gly Asn Gly Cys Phe Glu Xaa Tyr His
                485                 490                 495

Lys Cys Asp Xaa Xaa Cys Ile Glu Ser Xaa Arg Asn Gly Thr Tyr Xaa
            500                 505                 510

Xaa Xaa Lys Tyr Arg Xaa Glu Ser Xaa Leu Xaa Arg Xaa Lys Ile Xaa
        515                 520                 525

Gly Val Lys Leu Glu Ser Xaa Gly Xaa Tyr Xaa Ile Leu Xaa Ile Tyr
    530                 535                 540

Ser Thr Val Xaa Ser Ser Leu Val Leu Xaa Xaa Xaa Xaa Xaa Ala Phe
545                 550                 555                 560

Xaa Xaa Trp Ala Cys Ser Asn Gly Ser Xaa Arg Cys Asn Ile Cys Ile
                565                 570                 575
```